United States Patent [19]

Hinman et al.

[11] Patent Number: 6,015,562
[45] Date of Patent: Jan. 18, 2000

[54] TARGETED FORMS OF METHYLTRITHIO ANTITUMOR AGENTS

[75] Inventors: Lois M. Hinman, Sleepy Hollow; Philip R. Hamann, Garnerville, both of N.Y.

[73] Assignee: American Cyanamid Company, Madison, N.J.

[21] Appl. No.: 08/603,024

[22] Filed: Feb. 16, 1996

Related U.S. Application Data

[63] Continuation of application No. 08/332,025, Oct. 31, 1994, abandoned, which is a continuation-in-part of application No. 08/132,725, Oct. 6, 1993, abandoned, which is a continuation-in-part of application No. 07/948,277, Sep. 22, 1992, abandoned.

[51] Int. Cl.[7] .................................................. A61K 39/395
[52] U.S. Cl. ..................................... 424/181.1; 424/179.1; 424/178.1; 514/12; 514/25; 514/26; 530/391.9; 530/391.7
[58] Field of Search .................................. 514/2, 12, 25, 514/26; 424/181.1, 179.1, 178.1; 530/391.7, 391.9

[56] References Cited

U.S. PATENT DOCUMENTS 5,053,394  10/1991  Ellestad et al. ........................... 514/24

FOREIGN PATENT DOCUMENTS 0 392 384 A2  10/1990  European Pat. Off. .

OTHER PUBLICATIONS

Hird, V., et al., Immunotherpay with Monoclonal Antibodies. In:Genes and Cancer, Carney et al. (ed.) Wiley & Sons, 1990.
Queen C., et al., A humanized antibody that binds to the interleukin 2 receptor. Proc. Natl. Acad. Sci. vol. 86, pp. 10029–10033, 1989.
Riechman, L., et al., Reshaping human antibodies for therapy. Nature. vol. 332, pp. 323–327. 1988.
Waldmann, T.A., Monoclonal Antibodies in Diagnosis and Therapy. Science. vol., 252, pp. 1657–1662. 1991.

*Primary Examiner*—Keith D. MacMillan
*Assistant Examiner*—J. D. Wessendorf

[57] ABSTRACT

The invention is humanized CT-M-01 monoclonal antibody molecule-drug conjugates prepared from the family of methyltrithio antitumor agents.

29 Claims, 16 Drawing Sheets

TARGETED FORMS OF METHYLTRITHIO ANTITUMOR AGENTS

This application is a continuation of U.S. Ser. No. 08/332,025 filed Oct. 31, 1994, now abandoned, which is a continuation-in-part application of co-pending U.S. Ser. No. 08/132,725 filed Oct. 6, 1993, now abandoned, which is a continuation in part of U.S. Ser. No. 07/948,277 filed Sep. 22, 1992, now abandoned.

SUMMARY OF THE INVENTION

The invention is carrier-drug conjugates of the disulfide analogs of the $\alpha_1$, $\alpha_2$, $\alpha_3$, $\alpha_4$, $\beta_1$, $\beta_2$, $\gamma_1$, $\delta_1$ and pseudoaglycone components of the LL-E33288 complex and derivatives thereof, as well as the disulfide analogs of BBM-1675, FR-900405, FR-900406, PD 114759, PD 115028, CL-1577A, CL-1577B, CL-1577D, CL-1577E and CL 1724 antitumor antibiotics and derivatives thereof. The carrier portion of the conjugate is the humanized CT-M-01 monoclonal antibody.

DETAILED DESCRIPTION OF THE INVENTION

Figure 1:
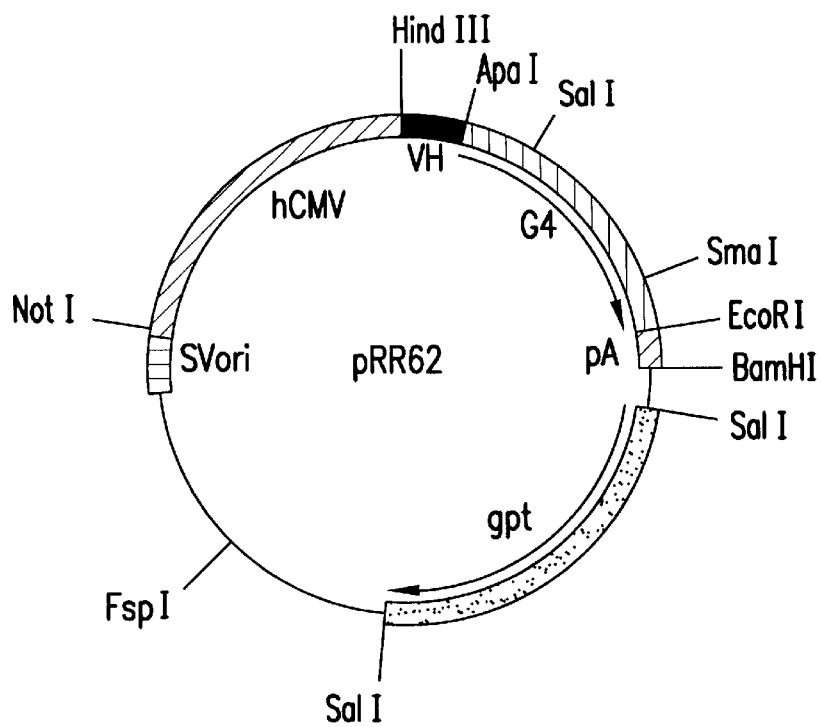
FIG. 1 is a schematic diagram of plasmid pRR62.

Target forms of methyltrithic antitumor agents are disclosed in U.S. Pat. No. 5,053,394 (1991). Carrier-drug conjugates where the murine monoclonal antibody CT-M-01 are also disclosed.

The family of antibacterial and antitumor agents, known collectively as the LL-E33288 complex are described and claimed in U.S. Pat. No. 4,970,198 (1990) and are used to prepare the disulfide antitumor agents which are some of the starting materials for targeted forms of the antitumor agents of our invention.

U.S. Pat. No. 4,970,198 application describes the LL-E33288 complex, the components thereof, namely, LL-E33288$\alpha_1^{Br}$, LL-E33288$\alpha_1^I$, LL-E33288$\alpha_2^{Br}$, LL-E33288$\alpha_2^I$, LL-E33288$\alpha_3^{Br}$, LL-E33288$\alpha_3^I$, LL-E33288$\alpha_4^{Br}$, LL-E33288$\beta_1^{Br}$, LL-E33288$\beta_1^I$, LL-E33288$\beta_2^{Br}$, LL-E33288$\beta_2^I$, LL-E33288$\delta_1^{Br}$, LL-E33288$\delta_1^I$, LL-E33288$\delta_1^I$, and methods for their production by aerobic fermentation utilizing a new strain of *Micromonospora echinospora ssp calichensis* or natural or derived mutants thereof. U.S. Pat. No. 4,970,198 also discloses proposed structures for some of the above-named components.

Additional members of the LL-E33288 complex (the calicheamicins) are described and claimed in U.S. Pat. No. 4,939,244 (1990) and are likewise useful for preparing the targeted forms of the antitumor agents of our invention. This application also describes the LL-E33288 bromo- and iodo-pseudoaglycones of the series, which have been prepared by chemical means. The application also described dihydro derivatives accessable from all the above-named antitumor antibiotics through sodium borohydride reduction of the ketone at $C_{11}$ to a hydroxyl group.

Still other members of the LL-E33288 family of antitumor antibiotics are described and claimed in U.S. Pat. No. 5,079,233 (1992), and also are useful for preparing additional targeted forms of the antitumor agents of our invention. This application describes N-acyl derivatives of several members of the LL-E33288 complex which have been prepared by chemical means.

Other antibiotics are useful in our inventions, namely:
1) Esperamicin BBM-1675, a novel class of potent antitumor antibiotics. I. Physico-chemical data and partial structure. M. Konishi, et. al., J. Antibiotics, 38, 1605 (1985). A new antitumor antibiotic complex, M. Konishi, et. al., U.K. Patent Application BG 2,141, 425A, May 15, 1984 and U.S. Pat. No. 4,675,187 (1987).
2) New antitumor antibiotics, FR-900405 and FR-900406. I. Taxonomy of the producing strain. M. Iwami, et. al., J. Antibiotics, 38, 835 (1985). New antitumor antibiotics FR-900405 and FR-900406. II. Production, isolation, characterization and antitumor activity. S. Kiyoto, et. al., J. Antibiotics, 38, 340 (1985).
3) PD 114759 and PD 115028, novel antitumor antibiotics with phenomenal potency. I. Isolation and characterization. R. H. Bunge, et. al., J. Antibiotics, 37, 1566 (1984) U.S. Pat. No. 4,554,162 (1985). Biological and biochemical activities of the novel antitumor antibiotic PD 114759 and related derivatives. D. W. Fry et. al., Investigational New Drugs, 4, 3 (1986).
4) New antibiotic complex CL-1577A, CL-1566B produced by Streptomyces asp. ATCC 39363. U.S. Pat. No. 4,539,203 (1985).
5) CL-1577D and CL-1577E Antibiotic antitumor compounds, their production and use. U.S. Pat. No. 4,539,203.

6) CL-1724 Antibiotic compounds, their production and use. U.S. Pat. No. 4,554,162.
7) New antitumor antibiotics BBM-1675-A3 and BBM-1675-A4, obtained by fermentation of actinomadura verrucosospora strains H964-92 (ATCC 39334) or AB27Y (ATCC 39638). U.S. Pat. No. 4,675,187.
8) New N-acetyl-esperamicin $A_1$, $A_2$ and $A_{1\beta}$ derivatives with antimicrobial and antitumor activities. U.S. Pat. No. 4,837,206.

All of the information regarding the LL-E33288 family of antitumor antibiotics, BBM-1675, FR-900405, FR-900406, PD 114759, PD 115028, CL-1577A, CL-1577B, CL-1577D, CL-1577E and CL-1724 contained in the above citations is incorporated herein by reference. The $\alpha_1$, $\alpha_2$, $\alpha_3$, $\alpha_4$, $\beta_1$, $\beta_2$, $\gamma_1$, $\delta$, and pseudoaglycone components of the LL-E33288 complex their dihydro and N-acyl counterparts, as well as the BBM-1675, FR-900405, FR-900406, PD 114759, PD 115028, CL-1577A, CL-1577B, CL-1577D, CL-1577E and CL-1724 antibiotics and their N-acyl counterparts, each contain a methyltrithio group in their structure. The methyltrithio moiety of the above-named antibiotic is subject to displacement by a variety of thiol-containing organic molecules resulting in the formation of a new class of anticancer and antibacterial agents as described U.S. Pat. Nos. 5,606,040 and 5,770,710. Displacement of the methyltrithio unit of the antitumor antibiotics as depicted in Scheme I, below, can be used to introduce a spacer (Sp), the judicious choice of which enables the introduction of humanized CT-M-01 monoclonal antibody (hereinafter hu:CT-M-01) into the compounds of the above-named patents and applications.

Scheme I

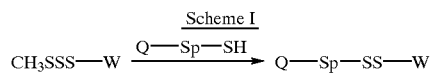

With reference to Scheme I $CH_3$—SSS—W is the antitumor antibiotic, Sp is a straight or branched-chain divalent or trivalent ($C_1$–$C_{18}$) radical, divalenrt or trivalent aryl or heteroaryl radical, divalent or trivalent ($C_3$–$C_{18}$) cycloalkyl or heterocycloalkyl radical, divalent or trivalent aryl- or heteroaryl-alkyl ($C_1$–$C_{18}$) radical, divalent or trivalent cycloalkyl- or heterocycloalkyl-alkyl ($C_1$–$C_{18}$) radical, or divalent or trivalent ($C_2$–$C_{18}$) unsaturated alkyl radical, wherein if Sp is a trivalent radical, it can be additionally substituted by amino, alkylamino, arylamino, heteroarylamino, carboxyl, lower alkoxy, hydroxy, thiol or lower alkylthio groups; Q is, or can be subsequently converted to, halogen, amino, alkylamino, carboxyl, carboxaldehyde, hydroxy, thiol, α-haloacetyloxy, lower alkyldicarboxyl, —CONHNH$_2$, —NHCONHNH$_2$, —NHCSNHNH$_2$, —ONH$_2$, —CON$_3$,

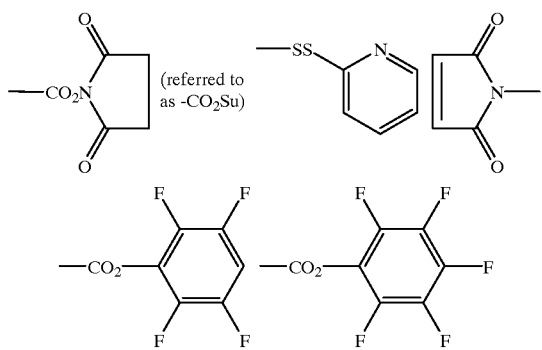

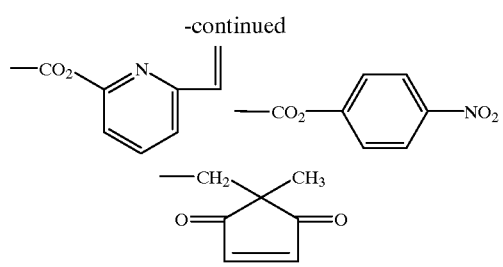

As long as the product from Scheme I contains at least one functional group which can be converted to, or is directly reactive with a targeting unit (hu:CT-M-01), targeted forms of the antitumor antibiotics of the above-named patents and applications can be generated, as shown in Scheme II below:

Scheme II

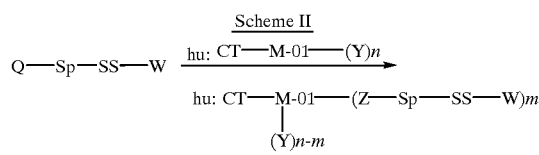

wherein Q, Sp, and W are as hereinbefore defined, hu:CT-M-01 is the humanized monoclonal antibody, its fragments, or its chemically manipulated counterparts; Y is a side-chain amino, carboxy, or thiol group of a protein, an aldehyde derived from carbohydrate residues, or an amidoalkylthio group; n is an integer of from 1 to 100; Z is formed from covalent reaction of the groups Q and Y directly or after subsequent reduction and Z is —CONH—, —CONHN═CH—, —CONHNHCH$_2$—, —NH—CONHN═CH—, —NHCONHNHCH$_2$—, —NHCSNHN═CH—, —NHCSNHNHCH$_2$—, —ON═CH—, —NH—, —NHCH$_2$—, —N═CH—, —CO$_2$—, —NHCH$_2$CO$_2$—, —SS—,

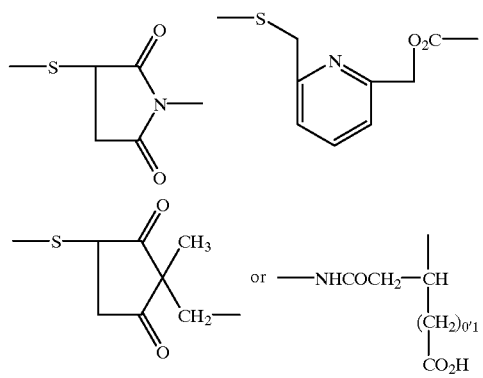

and m is 0.1 to 15.

As an example, and with reference to Scheme II, above, the 3-mercaptopropionic acid derivative of E-33288$\gamma_1^I$ (Q═CO$_2$H, Sp═—CH$_2$CH$_2$—), when converted to its activated hydroxysuccinimide form (Q═CO$_2$Su, Sp═—CH$_2$CH$_2$—) can be used to react with some of the ε-amino groups of lysine residues (e.g., Y═—NH$_2$ wherein n=50–100 from available lysine residues), at a pH between 7.0 and 9.5 in aqueous buffered solutions at temperatures between 4° C. to 40° C. to produce targeted forms of the antibiotics attached at random sites along the protein backbone (Z═—NHCO—, Sp═—CH$_2$CH$_2$, m=1–10). Only a fraction of the available lysine residues are substituted in this manner, since high loading is generally not considered compatible with preserving the antibody immunoreactivity. The same randomly-substituted immunoconjugates can also be prepared from the 3-mercaptopropionic acid derivative using other carhoxyl group activating agents such as a variety of carbodiimides, or the corresponding acyl azide. Alternatively, a 3-mercaptopropic,nyl hydrazide derivative of E-33288$\gamma_1^I$ (Q=$H_2NNHCO$—, Sp=—$CH_2CH_2$—), when reacted with a periodate-oxidized antibody (Y=—CHO, N=1–15) as described in U.S. Pat. No. 4,671,958 at a pH between 4 and 7, in a buffered aqueous solution at a temperature of between 4° C. and 40° C., reacts only at the aldehyde functionality (derived from cleavage of vic-diols of carbohydrate residues situated on the Fc portion of the antibodies) to generate hu:CT-M-01 conjugates containing the drug substituted at specific sites along the backbone of the protein (Z=—CH═NNHCO—, Sp=—$CH_2CH_2$—, m=0.5–10). Other aldehyde-reactive groups as part of the drug construct are within our invention to generate the products of Scheme II. Such functional groups are preferably, though not limited to, those which react with aldehydes under acidic aqueous conditions. The reactivity of protein lysines under basic conditions is sufficiently great such that their amines compete with the products of Scheme II for available aldehydes of the monoclonal antibody. Alternative aldehyde-reactive groups are for example, the semicarbazide, the thiosemicarbazide, and the O-substituted hydroxylamine functionalities.

Assembly of targeted forms of $CH_3$—SSS—W is not restricted to the sequence outlined in Scheme II. The hu:CT-M-01 targeting unit can be first modified to contain a thiol group, which is then reacted with the antitumor antibiotics useful in the invention in accordance with Scheme III below:

Scheme III 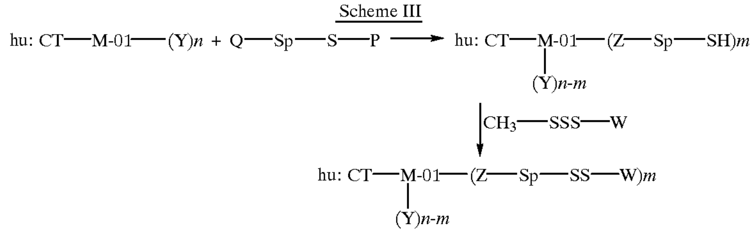 wherein Y, Q, Sp, W, n, and m are as hereinbefore defined, and P is hydrogen or 2-(pyridylthio), with the proviso that when Y is a thiol derived from a backbone amino acid residue of hu:CT-M-01, Z—Sp taken together is a covalent bond.

As an example, and with references to Scheme III, above, the hu:CT-M-01 monoclonal antibody can be reacted with 3-(2-dithiopyridyl)-propionic acid hydroxysuccinimide ester to modify the protein through lysine residues (Y=$NH_2$, n=50–100, Q=—$CO_2$Su, Sp=—$CH_2CH_2$—, P=2-pyridylthio). Following reduction with, for example, dithiothreitol, an intermediate is generated (Z=—NHCO—, Sp=—$CH_2CH_2$—, P=H, m=1–15) which can be reacted with the antitumor antibiotics to generate the subject immunoconjugates. Similarly, 2-iminothiolane can be reacted with hu:CT-M-01 to introduce thiol groups onto the surface of the protein directly, without requiring a reduction step (Z=—NHCO—, Sp=—$(CH_2)_3$—, P=H, m=1–15), and this intermediate can be reacted with the $CH_3$—SSS—W as before. Alternatively, sulfhydryl groups inherent within the structure of hu:CT-M-01 in dimeric form as cystine residues can be used to participate in the reaction of Scheme III directly. Such sulfhydryls are traditionally exposed by a combination of enzymatic digestion and reduction of native monoclonal antibodies (hu:CT-M-01=Fab' fragment, Z—Sp=Bond, Y=SH).

A preferred embodiment of this invention is a protein-drug conjugate of the formula:

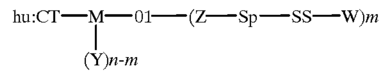

prepared from the class of antitumor antibiotics designated LL-E33288 ($CH_3$—SSS—W) comprising:

displacing the dithiomethyl moiety with a compound of formula Q—Sp—SH, wherein Sp is straight or branched-chain divalent or trivailent ($C_2$–$C_{10}$) radicals or divalent or trivalent ($C_2$–$C_5$) arylalkyl or heteroarylalkyl radicals, wherein if Sp is a trivalent radical, it can be additionally substituted by amino, heteroarylamino, hydroxy, or thiol groups; and Q is carboxyl, lower alkyldicarboxyl anhydride, —$CO_2$Su, —$CONHNH_2$, or 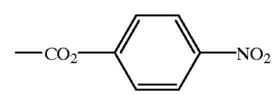 to produce an intermediate of general formula Q—Sp—SS—W, wherein Q, Sp, and W are as hereinbefore defined, and reacting Q—Sp—SS—W with a molecule of the formula hu:CT-M-01-$(Y)_n$ wherein Y is a side-chain amino group on the antibody, or an aldehyde generated by oxidation of the carbohydrate groups of the antibody, and n is an integer of from 1 to 100, to produce a compound of the formula:

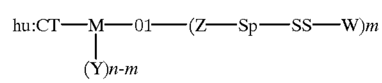

wherein Y, Sp, W, and n are as hereinbefore defined, and Z is formed from covalent reaction of the groups Q and Y directly or after subsequent reduction, and Z is —CONH—, —CONHN═CH—, —CONHNHCH$_2$—, or

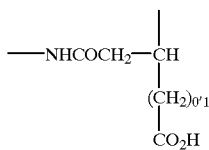

and m is 0.1 to 15.

The murine CT-M-01 is taught in Trouet et al.'s French Patent 85-10234 (1989). The humanized CT-M-01 "hu:CT-M-01" is taught in International Patent Application No. PCT/GB92/01759 (International Publication No. WO 93/06231) which is hereby incorporated by reference in its entirety.

The term "hu:CT-M-01" is used to describe a molecule having an antigen binding site derived from an immunoglobulin from a non-human species, the remaining immunoglobulin-derived parts of the molecule being derived from a human immunoglobulin. The antigen binding site may comprise: either a complete variable domain from the non-human immunoglobulin fused onto one or more human constant domains; or one or more of the complementarity determining regions (CDRs) grafted onto appropriate human framework regions in the variable domain. The abbreviation "MAb" is used to indicate a monoclonal antibody.

Since most MAbs in research or development are of rodent origin, they are naturally antigenic in humans and thus can give rise to an undesirable immune response termed the HAMA (Human Anti-Mouse Antibody) response. Therefore, the use of rodent MAbs as therapeutic agents in humans is inherently limited by the fact that the human subject will mount an immunological response to the MAb and will either remove the MAb entirely from circulation or at least reduce its effectiveness.

Therefore proposals have been made for making non-human MAbs less antigenic in humans. Such techniques can be generically termed "humanization" techniques. These techniques generally involve the use of recombinant DNA technology to manipulate DNA sequences encoding the polypeptide chains of the antibody molecule.

Early methods for humanizing MAbs related to production of chimeric antibodies in which an antigen binding site comprising the complete variable domains of one antibody are fused to constant domains derived from a second antibody. Methods for carrying out such chimerizations procedures are described in U.S. Pat. No. 4,861,397, U.S. Pat. No. 4,861,567, EP-A-0 171 496 (Res. Dev. Corp. Japan), EP 0173494 (Stanford University) and EP-A-0 194 276 (Celltech Limited).

EP-A-0 194 276 discloses a process for preparing an antibody molecule having the variable domains from a mouse MAb and the constant domains from a human immunoglobulin. It also describes the production of an antibody molecule comprising the variable domains of a mouse MAb, the $CH_1$ and $C_L$ domains of a human immunoglobulin, amnd a non-immunoglobulin-derived protein in place of the Fc portion of the human immunoglobulin.

Subsequently, a number of further patent applications have been published relating to chimeric antibodies, including tumor specific chimeric antibodies. Among these applications are WO-A-87/02671 (Int. Gen. Eng. Inc.), EP-A-0 256 654 (Centocor), U.S. Pat. No. 4,816,541, WO-A-89/00999 (Int. Gen. Eng. Inc.) and EP-A-0 332 424 (Hybritech Inc.).

Such humanized chimeric antibodies, however, still contain a significant proportion of non-human amino acid sequence, i.e., the complete variable domains. Thus, such humanized antibodies may elicit some HAMA response, particularly if administered over a prolonged period.

In an alternative approach, described in U.S. Pat. No. 5,225,539, the CDRs of a mouse MAb have been grafted onto the framework regions of the variable domains of a human immunoglobulin by site directed mutagenesis using long oligonucleotides. Such CDR-grafted humanized antibodies are less likely to give rise to a HAMA response than humanized chimeric antibodies in view of the lower proportion of non-human amino acid sequence which they contain. There are three CDRs (CDR1, CDR2 and CDR3) in each of the heavy and light chain variable domains.

The earliest work on CDR-grafted humanized MAbs was carried out on a MAb recognizing the synthetic antigen NP or NIP. However, subsequently, examples in which a mouse MAb recognizing lysozyme and a rat MAb recognizing an antigen on human T cells, respectively, were humanized have been described (Verhoeyen et al., Science, 293, 1534, 1988; Riechmann et al., Nature, 332, 323, 324, 1988). The preparation of the CDR-grafted antibody to the antigen on human T cells is also described in WO-A-89/07452 (Medical Research Council).

International Patent application No. PCT/GB90/02017 relates to the CDR-grafting of antibodies in general.

There have been a number of papers published concerning the production of chimeric monoclonal antibodies recognizing cell surface antigens. For instance, genetically engineered murine/human chimeric antibodies which retain specificity for tumor-associated antigens have been described (Sahagan et al, J. Immunol., 137, 3, 1066–1074, 1986 and U.S. Pat. No. 5,219,996). Also, a recombinant murine/human chimeric monoclonal antibody specific for common acute lymphocytic leukemia antigen has been described (Nishimura et al, Cancer Res., 47, 999–1005, 1987).

The hu:CT-M-01 MAbs to human milk fat globule (HMFG) derived from the anti-HMFG mouse MAb CT-M-01 (Aboud-Pirak et al, Cancer Res., 48, 3188–3196, 1988) have been prepared for the invention.

There is provided a hu:CT-M-01 having specificity for HMFG and having an antigen binding site wherein at least one of the CDRs of the variable domain is derived from the mouse monoclonal antibody CT-M-01 (CT-M-01 MAb) and the remaining immunoglobulin-derived parts of the hu:CT-M-01 are derived from a human immunoglobulin.

The hu:CT-M-01 may comprise a chimeric humanized antibody or a CDR-grafted humanized antibody. When the hu:CT-M-01 comprises a CDR-grafted humanized antibody, each heavy or light chain variable domain may comprise only one or two CT-M-01-derived CDRs. Preferably, however, all three heavy and light chain CDRs are derived from CT-M-01 MAb.

The CT-M-01 MAb is a mouse MAb of the type IgG1-kappa raised against the membrane-associated antigen of HMFG and has been extensively studied. The CT-M-01 MAb has been shown to recognize breast, ovarian and non-small cell lung cancers. It has been shown to internalize rapidly into target cells. Conjugates of CT-M-01 MAb and calicheamicin display highly specific cytotoxicity against appropriate cell lines (U.S. Pat. No. 5,053,394).

High levels of the antigen recognized by the CT-M-01 MAb have been detected circulating in the blood of patients suffering from breast cancer. This may have a deleterious effect on pharmacokinet.ics and tumor localization in vivo.

However, circulating antigen levels in the blood of patients suffering from ovarian cancer are lower than those in breast cancer patients. It is therefore believed that the hu:CT-M-01 of the present invention will be of particular use in the treatment of ovarian cancer.

Surprisingly, it has been found that humanizing the CT-M-01 MAb, in particular by CDR-grafting, does not substantially adversely affect its binding-activity and this produces a hu:CT-M-01 which is extremely useful in both therapy and diagnosis of certain carcinomas.

The hu:CT-M-01 of the present invention may comprise: a complete antibody molecule, having full length heavy and light chains; a fragment thereof, such as an Fab, Fab', (Fab')$_2$ or Fv fragment; a single chain antibody fragment, e.g., a single chain Fv; a light chain or heavy chain monomer or dimer; or a fragment or analogue of any of these or any other molecule with the same specificity as the CT-M-01 MAb.

The remaining non-CT-M-01 immunoglobulin-derived parts of the hu:CT-M-01 may be derived from any suitable human immunoglobulin. For instance, when the hu:CT-M-01 is a CDR-grafted hu:CT-M-01, appropriate variable region framework sequences may be used having regard to the class or type of the CT-M-01 donor antibody from which the antigen binding regions are derived. Preferably, the type of human framework used is of the same or similar class or type as the donor antibody (CT-M-01 is IgG1-kappa). Advantageously, the framework is chosen to maximize or optimize homology with the donor antibody sequence, particularly at positions spatially close to or adjacent to the CDRs. Examples of human frameworks which may be used to construct CDR-grafted hu:CT-M-01 are LAY, POM, TUR, TEI, KOL, NEWM, REI and EU (Kabat et al, Sequences of Proteins of Immunological Interest, U.S. Department of Health and Human Services, NIH, USA, 1987 and Wu, T. T. and Kabat, E. A., J. Exp. Med., 132, 211–250, 1970). KOL and NEWM are suitable for heavy chain construction. REI is suitable for light chain construction. EU is particularly suited for both heavy chain and light chain constructions. Preferably, the EU framework is used as the human framework for both heavy and light chain variable domains in view of its high level of homology with the CT-M-01 MAb.

The human constant domains of the hu:CT-M-01, where present, may be selected having regard to the proposed function of the antibody, in particular the effector functions which may be required. For example, the constant domains may be human IgA, IgG or IgM domains. IgG2 and IgG4 isotype domains may also be used.

The remainder of the hu:CT-M-01 need not comprise only protein sequences from human immunoglobulins. For instance, a gene may be constructed in which a DNA sequence encoding part of a human immunoglobulin chain is fused to a DNA sequence encoding the amino acid sequences of a polypeptide effector or reporter molecule.

A process for producing hu:CT-M-01 is as follows:
 (a) producing in an expression vector an operon having a DNA sequence which encodes an antibody heavy or light chain comprising a variable domain wherein at least one of the CDRs of the variable domain is derived from the CT-M-01 MAb and the remaining immunoglobulin-derived parts of the antibody chain are derived from a human immunoglobulin;
 (b) producing in an expression vector an operon having a DNA sequence which encodes a complementary antibody light or heavy chain comprising a variable domain wherein at least one of the CDRs of the variable domain is derived from the CT-M-01 MAb and the remaining immunoglobulin-derived parts of the antibody chain are derived from a human immunoglobulin;
 (c) transfecting a host cell with both operons; and
 (d) culturing the transfected cell line to produce the hu:CT-M-01.

The cell line may be transfected with two vectors, the first vector containing the operon encoding the light chain-derived polypeptide and the second vector containing the operon encoding the heavy chain-derived polypeptide. Preferably, the vectors are identical except in so far as the encoding sequences and selectable markers are concerned so as to ensure as far as possible that each polypeptide chain is equally expressed.

Alternatively, a single vector may be used, the vector including the operon encoding both light chain- and heavy chain-derived polypeptides.

In further aspects, the invention also includes DNA sequences coding for the heavy and light chains of the hu:CT-M-01 of the present invention, cloning and expression vectors containing these DNA sequences, host cells transformed with these DNA sequences and processes for producing the heavy or light chains and antibody molecules comprising expressing these DNA sequences in a transformed host cell.

The general methods by which the vectors may be constructed, transfection methods and culture methods are well known.

Preferably, the hu:CT-M-01 of the present invention is produced by recombinant DNA technology according to the following descriptions:

Molecular Cloning and Construction of the CT-M-O1 Chimeric Heavy Chain

The heavy chain variable domain of CT-M-O1 was cloned using the polymerase chain reaction. This enabled the construction of the chimeric version in a single step as described below.

Polyadenylated RNA was isolated from the CT-M-O1 hybridoma cell line using the guanidinium isothiocyanate/lithium chloride method (Maniatis et al, Molecular Cloning, Cold Spring Harbour, N.Y., 1982).

Double stranded cDNA was synthesised and used as a template for PCR amplification of the VH gene. A set of twenty four 5' forward primers were synthesized to complement a sequence within the murine leader sequence of VH domains (Kabat et al, Sequences of Proteins of Immunological Interest, U.S. Department of Health and Human Services, NIH, USA, 1987 and Wu, T. T. and Kabat, E. A. J. Exp. Med., 132, 211–250, 1970) and to introduce a BstEII restriction site. A set of twelve 3' reverse primers was synthesized to complement the framework 4 region of VH (Orlandi et al, Proc. Natl. Acad. Sci., USA, 86, 3833–3837, 1989) and included an ApaI restriction site.

The sequence of the basic 5' primer is given in the Sequence Listing as SEQ ID No: 5. The set of twenty four primers was based on this primer as follows. In one group of twelve primers, residue 27 remained as C. In three subgroups of four primers, residue 25 either remained as G or is altered to C or T. In each subgroup, the four primers differed at residue 28, which was A, C, G or T. In the subgroups where residue 25 is C or T, the sixth amino acid is His.

In the second group of twelve primers, residue 27 is changed to G. In three subgroups of four primers, residue 25 either remains as G or is altered to C or T. In each subgroup, the four primer differed at residue 28, which was A, C, G or T. Where residue 25 is C or G, amino acid 6 is Gln and where residue 25 is T, amino acid residue G is His. Where residue 28 is T or C, amino acid residue 7 is Cys. Where residue 28 is G, amino acid residue 7 is Trp.

The sequence of the basic 3' PCR primer is given in the Sequence Listing as SEQ ID No: 7. The set of twelve primers was based on this primer as follows. Residue 5 could remain as G or could be altered to A or T. Residue 11 either remains as A or is altered to G. Residue 12 either remains as A or is altered to C.

PCR amplification of CT-M-O1 VH was carried out using the following conditions:

10 pmoles each primer; 20 ng CDNA; 0.5 U Taq polymerase; 94° C. 1 min; 50° C. 2 min; 72° C. 3 min; for 40 cycles.

The PCR amplified VH fragment was restricted with BstEII and ApaI and ligated to an adaptor to reconstruct the leader sequence and add a 5' HindIII restriction enzyme site. The sequence of the adaptor used is given in the Sequence Listing as SEQ ID No: 8 and codes in part for the leader amino acid sequence of the VH domain of the murine anti TAG-72 monoclonal antibody B72.3 (U.S. Pat. No. 5,219, 996).

The adapted fragment was then cloned into the HindIII/ApaI sites of the vector pE1004 to give plasmid pRR62 shown in FIG. 1. Plasmid pRR62 consists of an SV40 origin of replication followed by the hCMV-MIE promoter/enhancer region. The promoter/enhancer controls a nucleotide sequence encoding a chimeric heavy chain comprising the CT-M-O1 heavy chain variable domain fused to human g4 constant domains. Downstream of the coding sequence is a poly A site and gpt gene.

The heavy chain variable region of several independent clones of pRR62 were sequenced. The DNA sequence and deduced amino sequence for CT-M-O1 VH are given in SEQ ID NOs: 1–2, respectively.

Molecular Cloning and Construction of the CT-M-O1 Chimeric Light Chain

Polyadenylated FNA was isolated from the CT-M-O1 hybridoma cell line using the guanidinium isothiocyanate/lithium chloride method (Maniatis et al, Molecular Cloning, Cold Spring Harbour, N.Y., 1982). Double stranded cDNA was synthesized (Gubler and Hoffman, Gene, 25, 263–269, 1983) and a cDNA library was constructed in plasmid pSP64 (22) using EcoRI linkers. A screening probe was synthesized, complementary to mouse immunoglobulin light chain constant region by PCR amplification. The light chain probe was a 318 bp PCR fragment encoding the mouse kappa light chain constant region (Max et al, J. Biol. Chem., 256, 5116–5120, 1981).

The probe was radiolabelled ($g^{32}P$) ATP by random hexanucleotide priming and was used to screen the cDNA library.

The clone which encoded the complete leader, variable and constant domains of light chain was isolated and designated as pRB63.

A fragment of pRB63, which encodes the variable domain of the light chain was recovered by PCR amplification. The PCR primers introduced a BstbI and SplI restriction sites at the 5' and 3' ends of the VL region respectively to enable subsequent cloning of the fragment.

Figure 2:
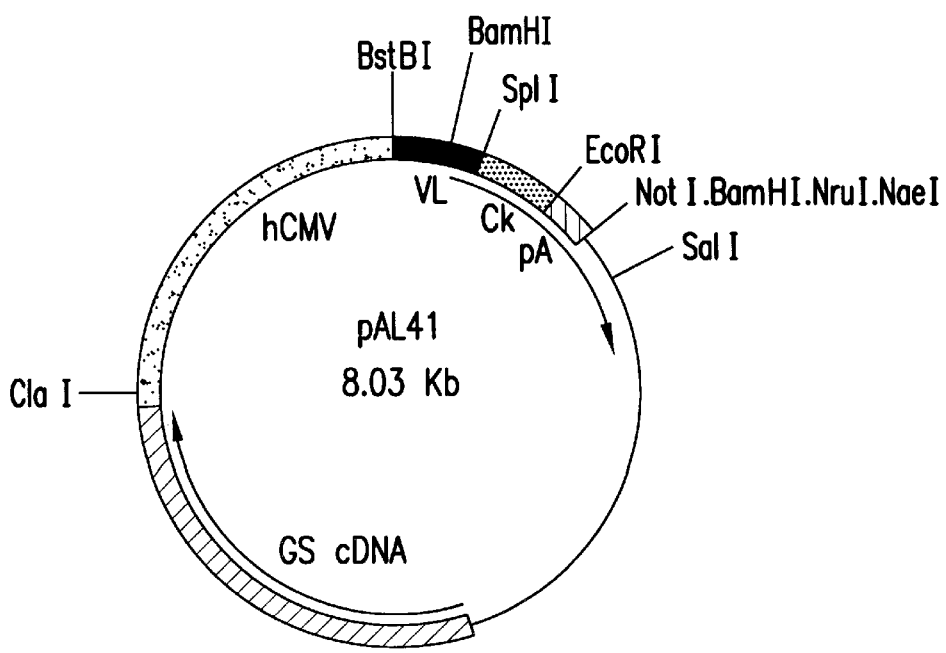
FIG. 2 is a schematic diagram of plasmid pAL41.

The PCR amplified fragment of plasmid pRB63 was restricted with BstbI/SplI and ligated between the BstbI/SplI sites of plasmid pMRR010 to produce plasmid pAL41, which is shown in FIG. 2. Plasmid pAL41 consists of a glutamine synthetase cDNA having downstream of it the hCMV-MIE promoter/enhancer region. The promoter/enhancer region controls a nucleotide sequence encoding a chimeric light chain comprising the CT-M-O1 light chain variable domain fused to a human CK constant domain. Downstream of the coding sequence is a poly A site.

Nucleotide sequence analysis was carried out according to the chain termination procedure (Sanger et al, PNAS, 74, 5463–5467, 1977). The VH coding sequence insert in pRR62 and the VL coding sequence insert in pAL41 were fully sequenced. The DNA and predicted amino acid sequences for the unprocessed variable domains of the CT-M-O1 heavy and light chains are shown in the Sequence Listing appended to the end of the description as SEQ ID NOs: 1–2 for the heavy chain, and SEQ ID NOs: 3–4 for the light chain.

SEQ ID No: 1 shows the sequence coding for the VH domain and SEQ ID NO: 2 shows the predicted amino acid sequence. The leader sequence for the heavy chain runs from residue 1 to residue 19 as shown in Sequence No. 1. SEQ ID No: 3 shows the sequence coding for the VL domain and SEQ ID NO: 4 shows the predicted amino acid sequence. The leader sequence for the light chain runs from residue 1 to residue 20 as shown in SEQ ID No: 3. Examination of the derived amino acid sequences revealed considerable homology with other characterized immunoglobulin genes. The CT-M-O1 MAb was confirmed to be an IgG1-kappa antibody.

Preparation of Chimeric Antibody Products
Chimeric Light Chain Vector

Figure 3:
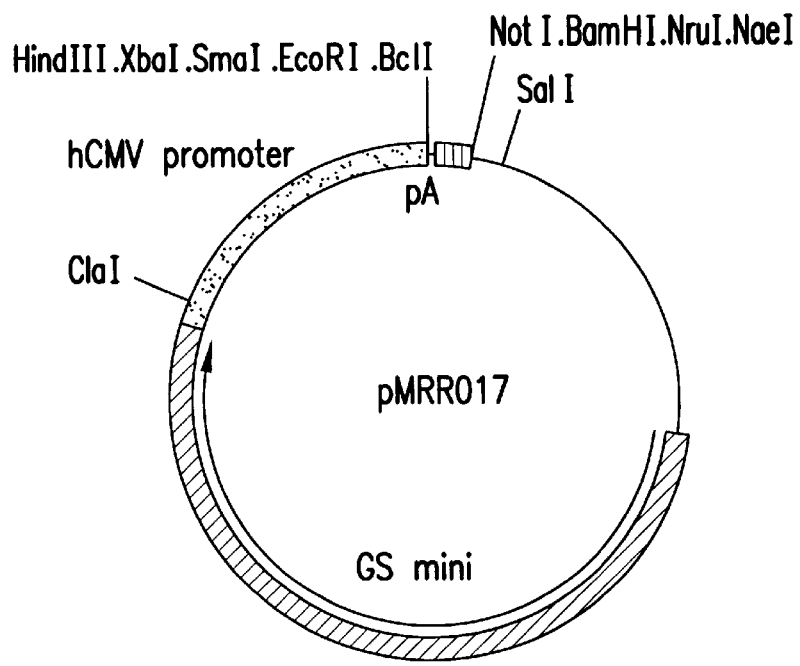
FIG. 3 is a schematic diagram of plasmid pMRR017.
Figure 4:
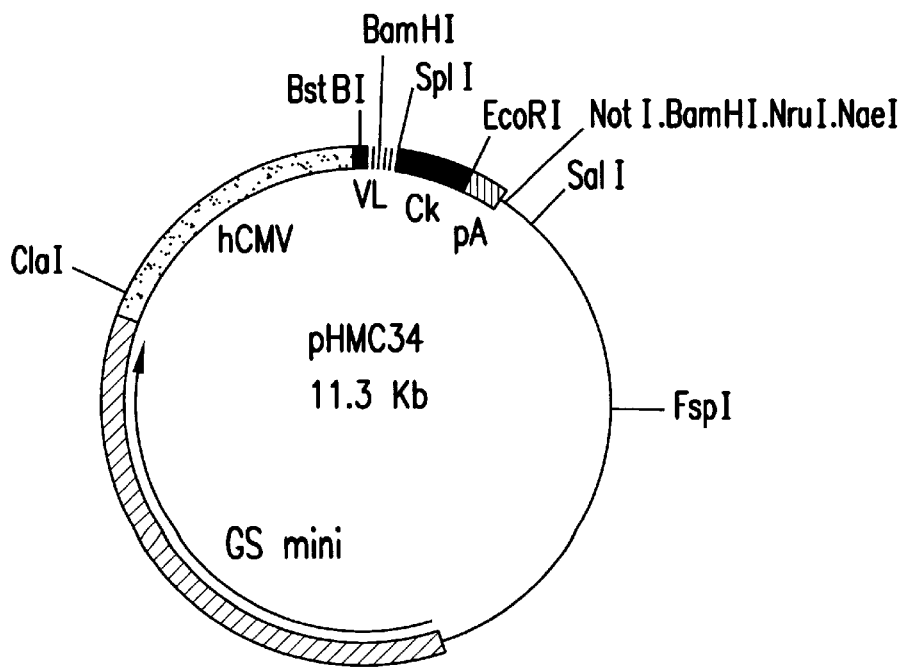
FIG. 4 is a schematic diagram of plasmid pHMC34.

A ClaI-EcoRI fragment of pAL41 carrying the hCMV promoter and chimeric light chain was cloned into plasmid pMRR017 which is shown in FIG. 3. Plasmid pMRR017 has a GS mini gene (WO-A-87/04462), hCMV-MIE promoter/enhancer region, a polylinker sequence and a poly A site. This produced plasmid pHMC34, which is shown in FIG. 4. In plasmid pHMC34, the chimeric light chain gene is under the control of the hCMV-MIE promoter/enhancer sequence.

Chimeric Heavy Chain Vectors

IgG1 Construct

Figure 5:
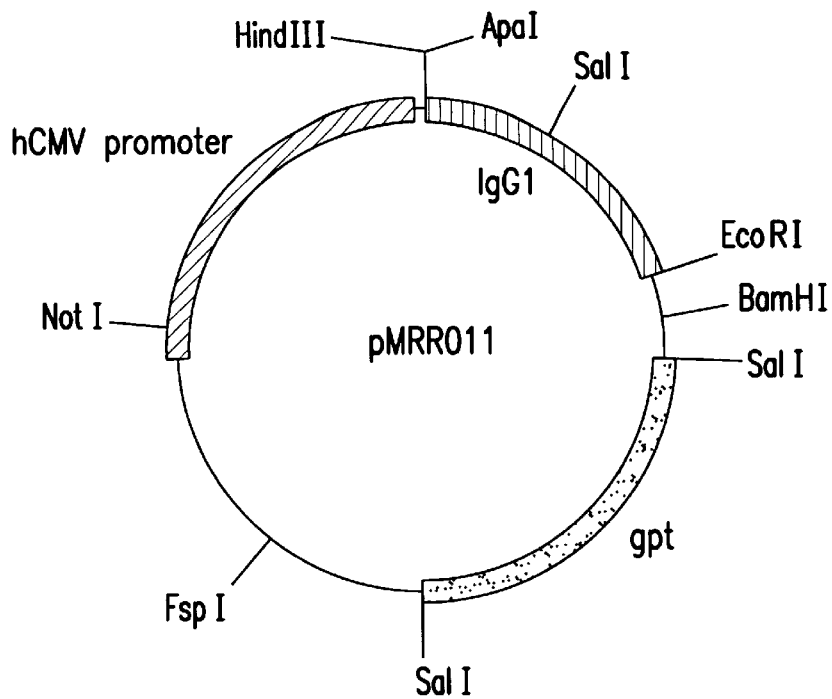
FIG. 5 is a schematic diagram of plasmid pMRR011.
Figure 6:
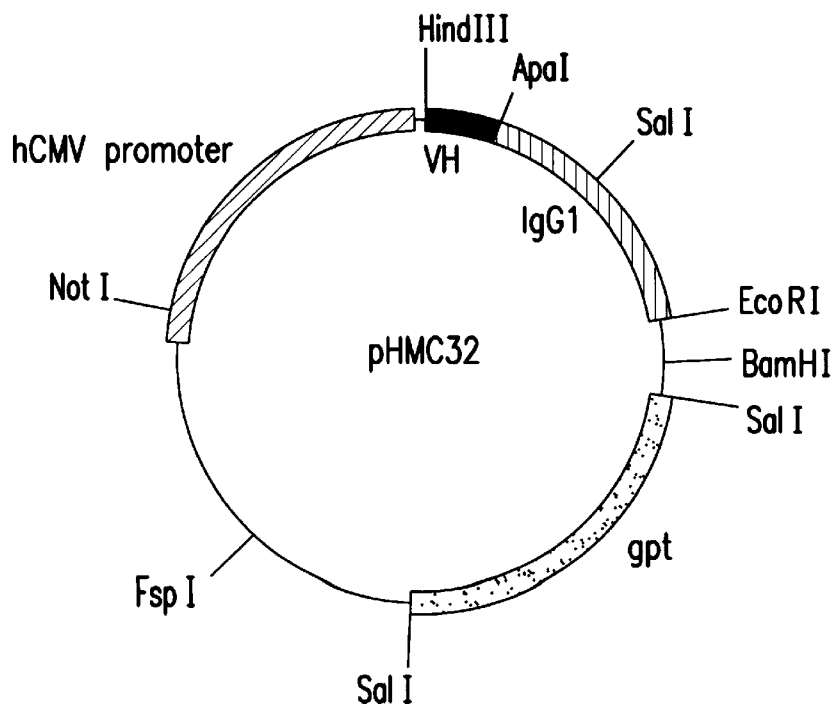
FIG. 6 is a schematic diagram of plasmid pHMC32.
Figure 7:
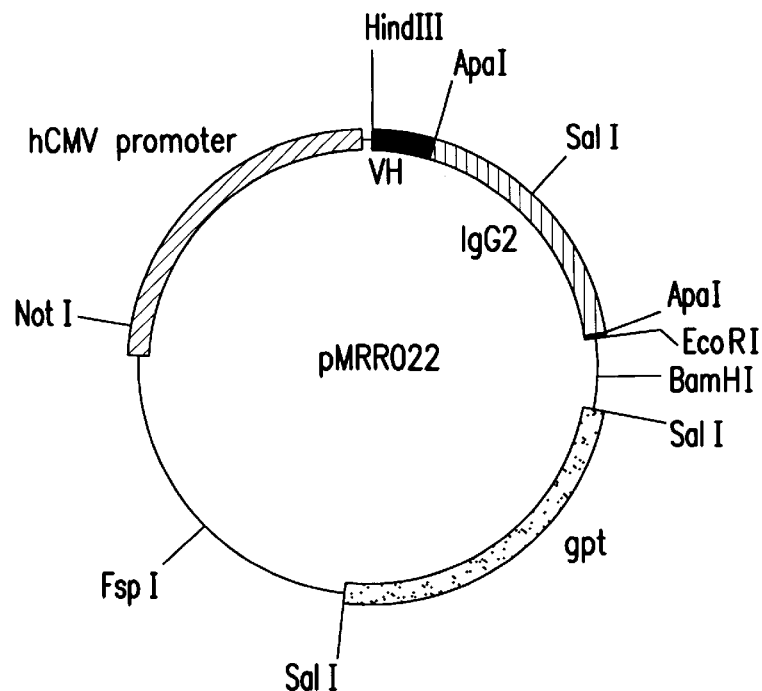
FIG. 7 is a schematic diagram of plasmid pMRR022.

A HindIII-ApaI fragment containing the sequence encoding the VH domain was excised from plasmid pRR62 (FIG. 1). This fragment was inserted between the HindIII and ApaI sites of plasmid pMRR011. Plasmid pMRR011 is shown in FIG. 5 and comprises an hCMV-MIE promoter/enhancer region, an SV40 polyadenylation sequence, a gpt gene and a sequence encoding a human IgG1 heavy chain lacking a variable domain. The plasmid thus produced, pHMC32, is shown in FIG. 6 and has a chimeric heavy chain coding sequence under the control of the hCMV-MIE promoter/enhancer. The chimeric heavy chain has the VH domain from the CT-M-O1 MAb fused to human IgG1 constant domains.

IgG2 Construct

The HindIII-ApaI fragment of pRR62 (FIG. 1) was inserted between the HindIII and ApaI sites of a plasmid containing an hCMV-MIE promoter, a polylinker site and a nucleotide coding sequence which encodes the three constant domains of a human IgG2 antibody. This yielded plasmid pMRR022 which encodes a chimeric heavy chain having the CT-M-O1 variable domain linked to the human IgG2 constant domains.

IgG4 Construct

Figure 8:
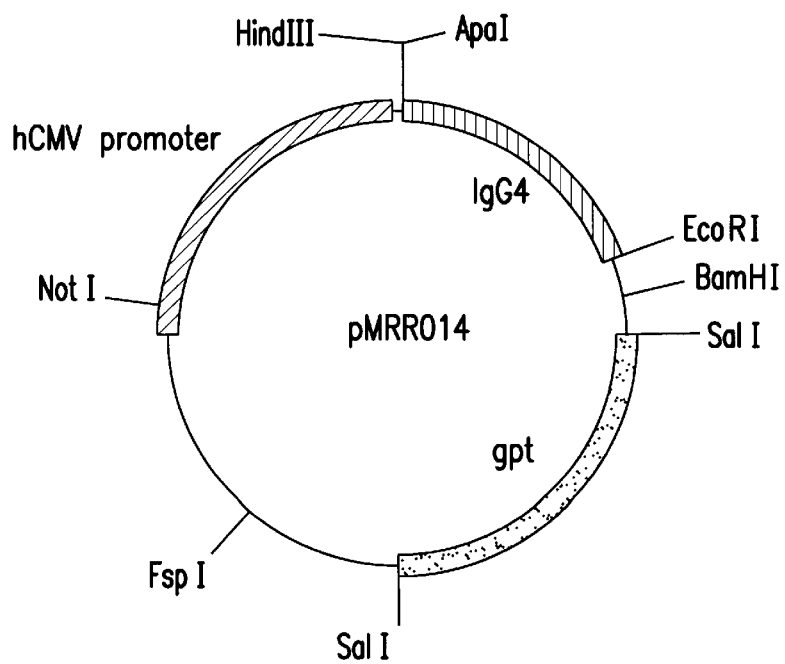
FIG. 8 is a schematic diagram of plasmid pMRR014.
Figure 9:
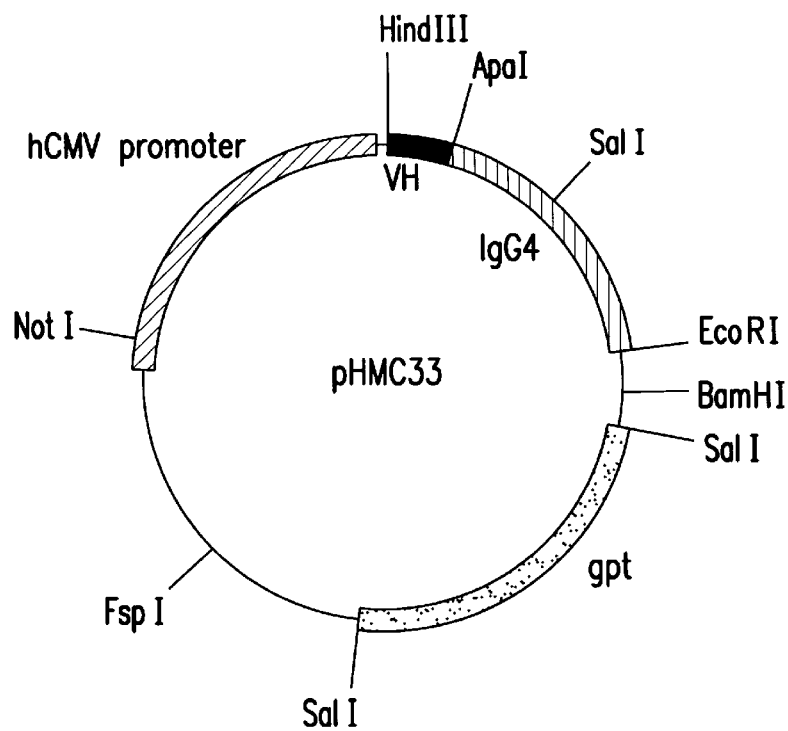
FIG. 9 is a schematic diagram of plasmid pHMC33.

The HindIII-ApaI fragment of pRR62 (FIG. 1) was inserted between the HindIII and ApaI sites of plasmid pMRR014 to produce plasmid pHMC33. Plasmids pMRR014 and pHMC33 are shown in FIGS. 8 and 9 respectively. Plasmid pMRR014 has an hCMV-MIE promoter, a polylinker site and a nucleotide coding sequence which encodes the three constant domains of a human IgG4 antibody. Plasmid pHMC33 is identical to plasmid pHMC32 except that the coding sequence encodes a chimeric heavy chain having the CT-M-O1 variable domain and human IgG4 constant domains in place of the human IgG1 constant domains.

Altered IgG4 Construct

Figure 10:
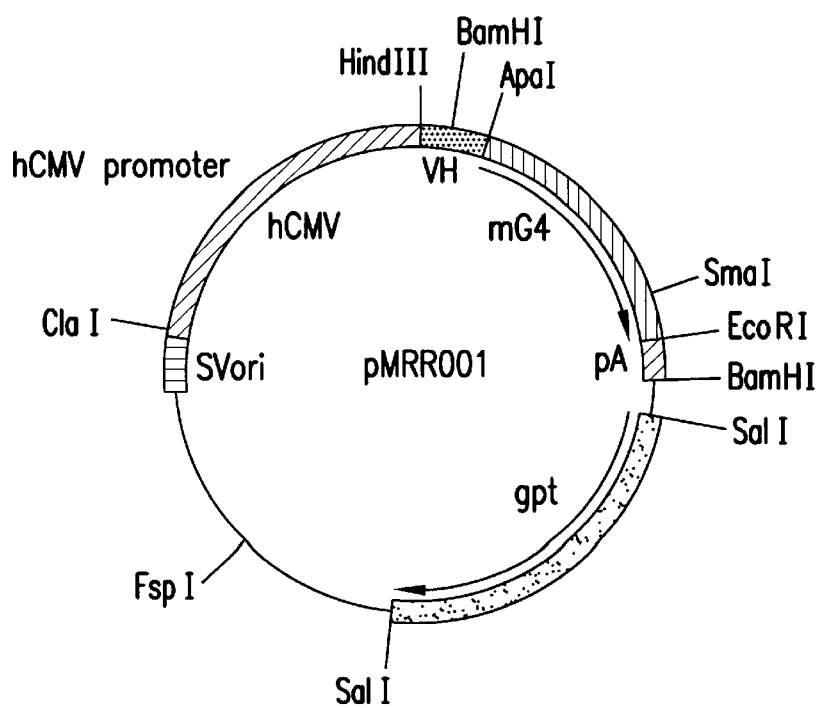
FIG. 10 is a schematic diagram of plasmid pMRR001.

The HindIII-ApaI fragment was reisolated from plasmid pHMC33. Plasmicd pMRR001 shown in FIG. 10 was digested with HindIII and ApaI. The large fragment was isolated and ligated to the HindIII-ApaI fragment of pHMC33 to produce plasmid pHMC35, shown in FIG. 11. Plasmid pHMC35 is almost identical to plasmid pHMC32 except that the coding sequence encodes a chimeric heavy chain having the CT-M-O1 variable domain and altered human IgG4 (hereinafter referred to as IgG4P) constant domains in place of the human IgG1 constant domains.

The alteration in the constant domains comprises a change of a serine residue in the hinge region at position 241 to a proline residue. This change advantageously abolished the formation of an 80 KD half antibody which otherwise occasionally is formed with IgG4 constant domains.

Chimeric Heavy and Light Chain Vectors

Vectlors were constructed having operons coding for both heavy and light chains within the same vector.

Figure 11:
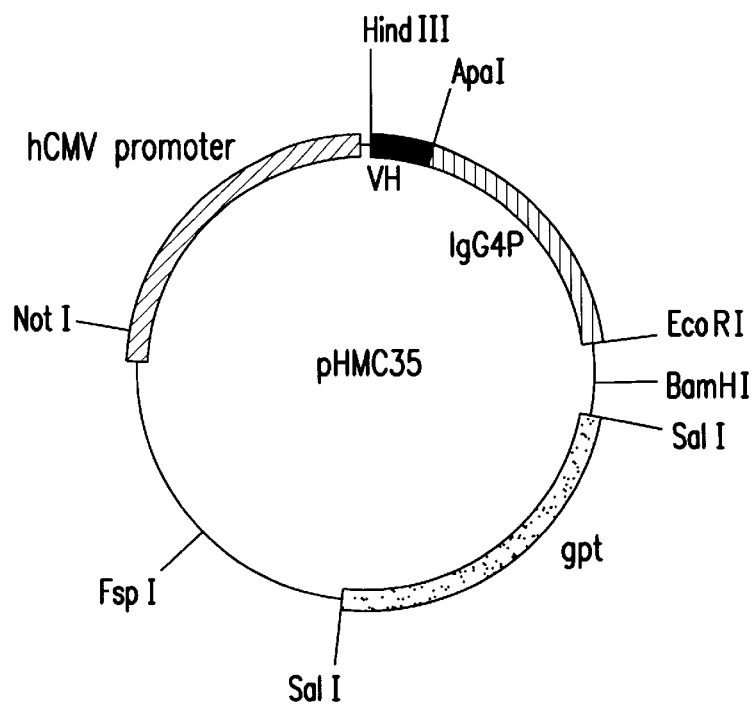
FIG. 11 is a schematic diagram of plasmid pHMC35.
Figure 12:
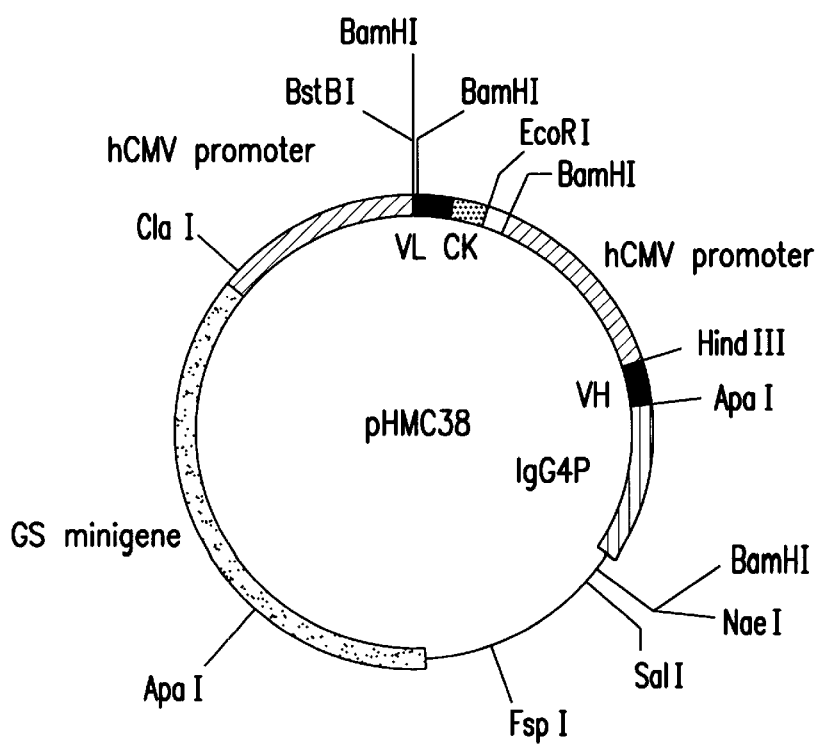
FIG. 12 is a schematic diagram of plasmid pHMC38.

A NotI-SalI fragment carrying the hCMV-MIE promoter/enhancer, the chimeric light chain encoding sequence and the Sv40 poly A site together with the GS mini gene was excised from plasmid pHMC34 (FIG. 4). A NotI-HindIII fragment carrying the hCMV-MIE prcmoter/enhancer was excised from plasmid pHMC35 (FIG. 11). A HindIII-SalI fragment carrying the altered IgG4 heavy chain coding sequence and SV40 poly A site was excised from plasmid pHMC35 (FIG. 11). These three fragments were ligated together to produce plasmid pHMC38, which is shown in FIG. 12, and codes for expression of chimeric light chain together with the altered IgG4 chimeric heavy chain.

Figure 14:
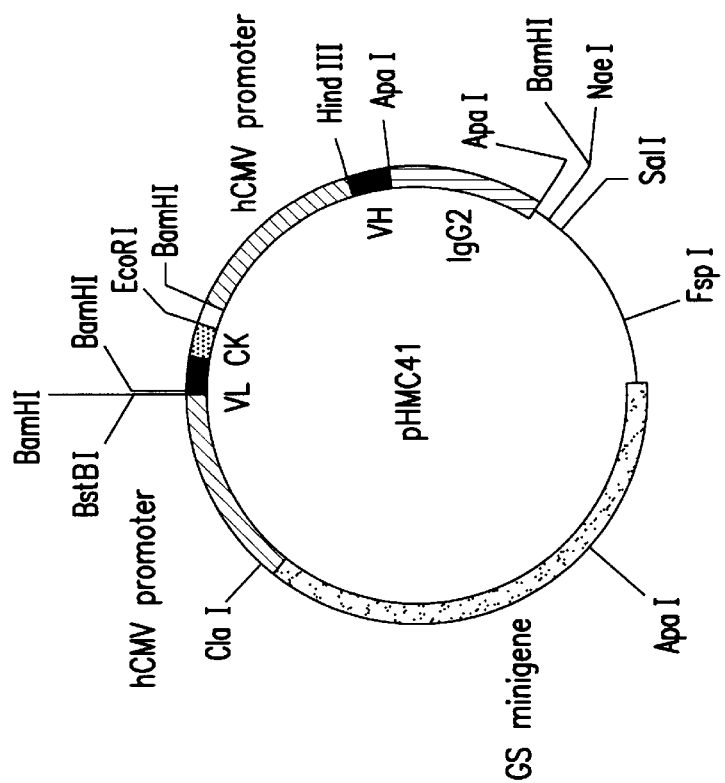
FIG. 14 is a schematic diagram of plasmid pHMC41.
Figure 13:
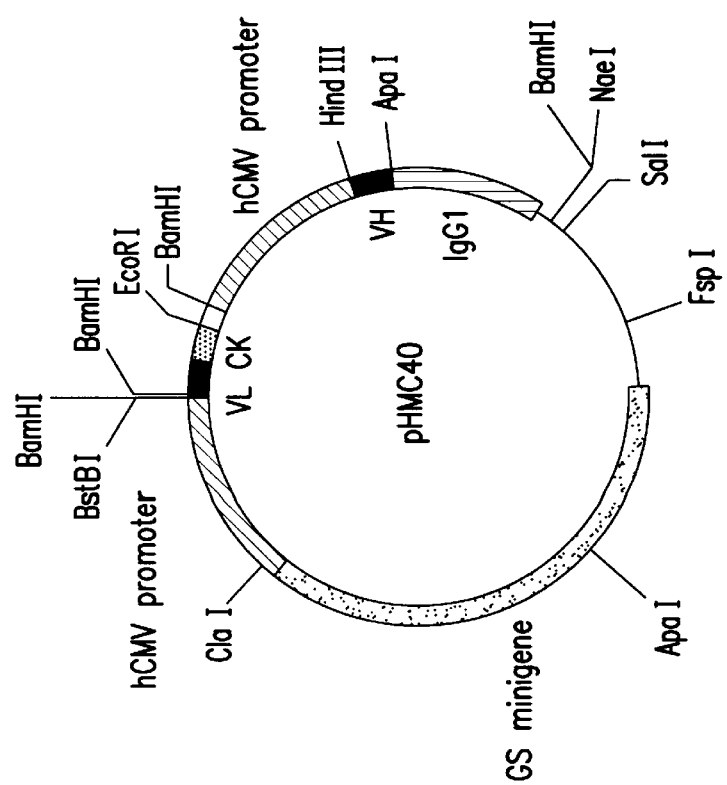
FIG. 13 is a schematic diagram of plasmid pHMC40.
Figure 15:
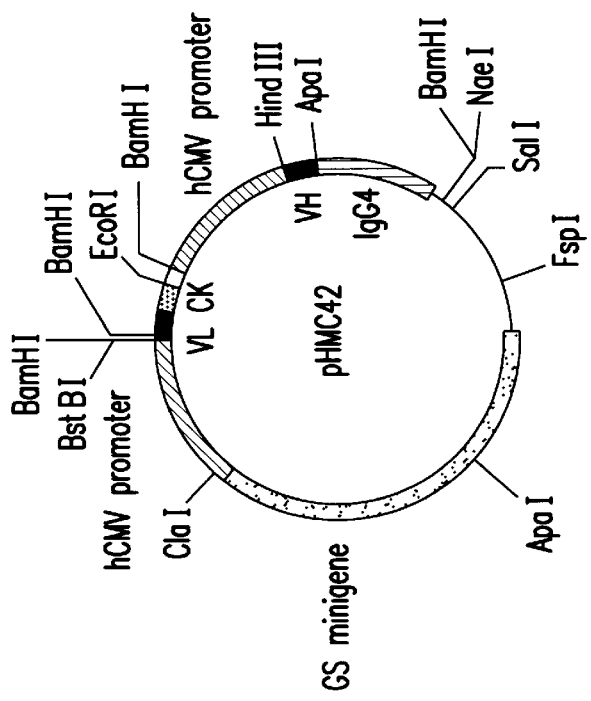
FIG. 15 is a schematic diagram of plasmid pHMC42.

Plasmids pHMC32, pMRR022 and pHMC33 were digested with HindIII and EcoRI and the fragments containing the chimeric heavy chain encoding sequences were isolated. The isolated fragments were each ligated with the large HindIII-SalI fragment of pHMC38 (FIG. 12) and an EcoRI-SalI fragment comprising the SV40 poly A region. The ligations produced plasmids pHMC40, pHMC41 and pHMC42 (shown in FIGS. 13 to 15 respectively). pHMC40 encodes a heavy chain having IgG1 constant domains. pHMC41 encodes IgG2 constant domains and pHMC42 encodes IgG4 constant domains.

Preparation of CDR-grafted Antibody Products

It was decided to use the EU human antibody framework (Kabat et al, Sequences of Proteins of Immunological Interest, U.S. Department of Health and Human Services, NIH, USA, 1987 and Wu, T. T. and Kabat, E. A. J. Exp. Med., 132, 211–250, 1970) for carrying out the CDR-grafting. The strategy followed for CDR-grafting was as set out in our International Patent Specification No. WO-A-91/09967.

Two CDR-grafted heavy chains were designed. In the first, gH1, all three CDRs (as defined by Kabat et al, Sequences of Proteins of Irnmmunological Interest, US Department of Health and Human Services, NIH, USA, 1987 and Wu, T. T. and Kabat, E. A. J. Exp. Med., 132, 211–250, 1970) were changed to murine residues. In addition, residues 2, 37, 71, 73, 94, 103, 104, 105 and 107, which are outside the Kabat CDRs, were also changed to murine residues. In the second, gH2, in addition to those murine residues in gH1, residues 48, 67 and 69 were changed to murine residues with a view to improving packing of the VH domain.

Two CDR-grafted light chains were also designed. In the first, gL1, all three CDRs (as defined by Kabat, et al, Sequences of Proteins of Immunological Interest, U.S. Department of Health and Human Services, NIH, USA, 1987 and Wu, T. T. and Kabat, E. A. J. Exp. Med., 132, 211–250, 1970) were changed to murine residues. In addition residues 3, 36, 63 and 108, which are outside the Kabat CDRs, were changed to murine resides. In the second, gL2, in addition to those murine residues in gL1, residues 37, 45 and 48 were changed to murine residues with a view to improving packing.

Figure 16:
FIG. 16 shows the alignment of oligonucleotides H1 to H8 in the formation of the gH1 coding sequence.

A nucleotide sequence coding for the gH1 variable domain was produced by oligonucleotide assembly using oligonucleotides H1 to H8. The sequences for these oligonucleotides are given in the Sequence Listing at the end of the description as SEQ ID NOS: 10 to 17. The way in which these oligonucleotides are assembled to produce the gH1 coding sequence is shown in FIG. 16. The amino acid sequence coded for by this gH1 sequence is shown in the sequence listing as SEQ ID NO: 18.

A nucleotide sequence coding for the gH2 variable domain was also produced by oligonucleotide assembly using oligonucleotides H1, H2, H3A, H4, H5, H6A, H7 and H8. Oligonucleotide H3A differs from oligonucleotide H3 (SEQ ID No: 12) in that residues 55 to 57 have been changed from GTG to GCA and residues 61 to 63 have been changed from ATT to CTG. Oligonucleotide H6A differs from oligonucleotide H6 (SEQ ID No: 15) in that residues 70 to 72 have been changed from TAC to TAA. Thus, the gH2 variable domain encodes the same sequence as is shown in SEQ ID NO. 18, except that at residue 67, MET has been changed to ILE; at residue 87, VAL has been changed to ALA; and at residue 89, ILE has been changed to LEU.

A nucleotide sequence coding for the gL1 variable domain was produced by oligonucleotide assembly using oligonucleotides L1 to L8. The sequences for these oligonucleotides are given in the Sequence Listing at the end of the description as SEQ ID Nos: 19–26. The way in which these nucleotides are assembled is similar to that shown in FIG. 16 for the gH1 coding sequence (except that L is substituted for H). The amino acid sequence coded for by the assembled gL1 variable domain coding sequence is shown in the Sequence Listing SEQ ID NO: 24.

A nucleotide sequence coding for the gL2 variable domain was produced by oligonucleotide assembly using oligonucleotides L1, L2A, L3A and L4 to L8. Oligonucleotide L2A differs from oligonucleotide L2 (SEQ ID NO. 20) in that residues 28 to 30 have been changed from CAG to GTA. Oligonucleotide L3A differs from oligonucleotide L3 (SEQ ID NO: 21) in that residues 25–27 have been changed from CAG to CTC, residues 49–52 have been changed from AAG to CAG and residues 59–61 have been changed from CAT to ATC. Thus, the gL2 variable domain encodes the same sequence as is shown: SEQ ID NO. 27, except that: at residue 23, Gln has been changed to Val; at residue 62, Gln has been changed to Leu; at residue 60, Lys has been changed to Gln; and at residue 73, Met has been changed to Ile.

For gene assembly 1 pmol of H2–H7 or L2–L7 was mixed with 10 pmol or H1 and H8 or L1 and L8 in a 100 ml reaction with 5U Taq polymerase. A PCR reaction was done using 30 cycles (95° C., 1 min. 50° C. 1 min; 72° C. 1 min). The resulting fragments were cut with HindIII and ApaI for VL with Bstb1 and SPlI for VH.

Figure 18:
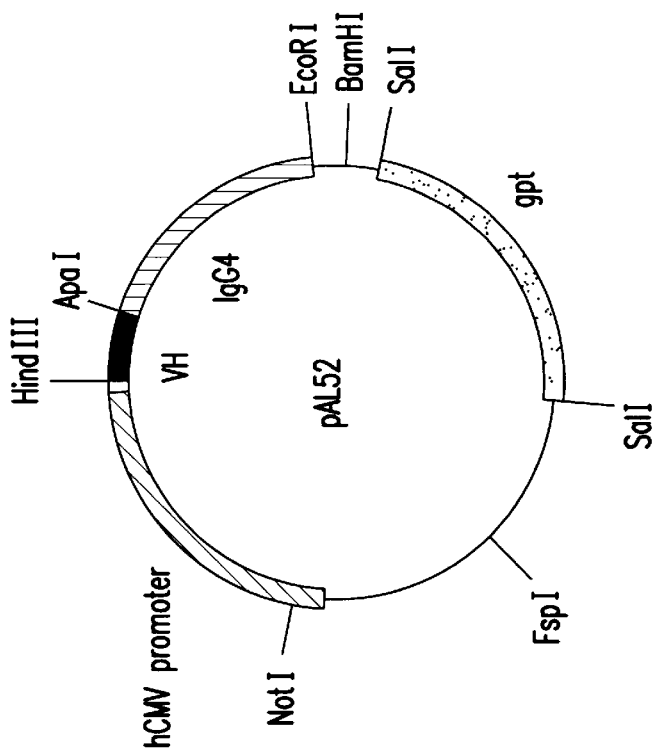
FIG. 18 is a schematic diagram of plasmid pAL52.
Figure 17:
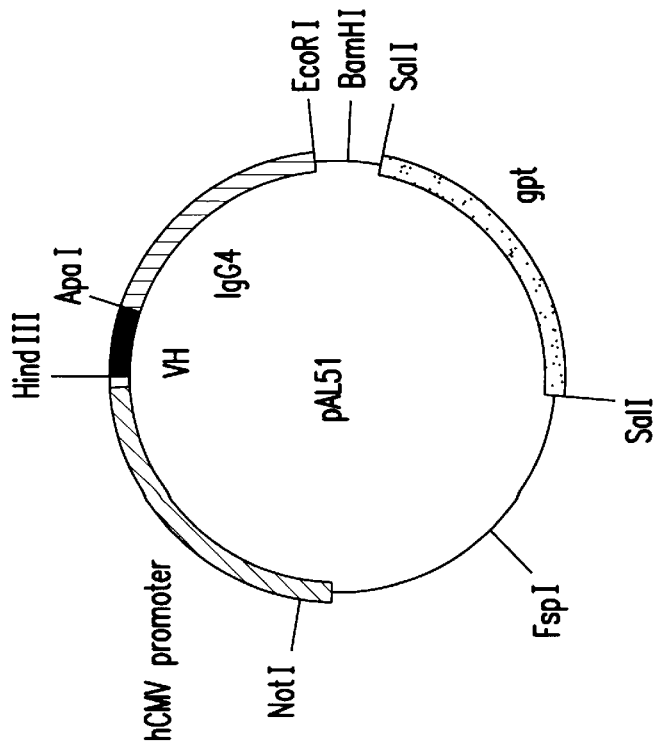
FIG. 17 is a schematic diagram of plasmid pAL51.
Figure 20:
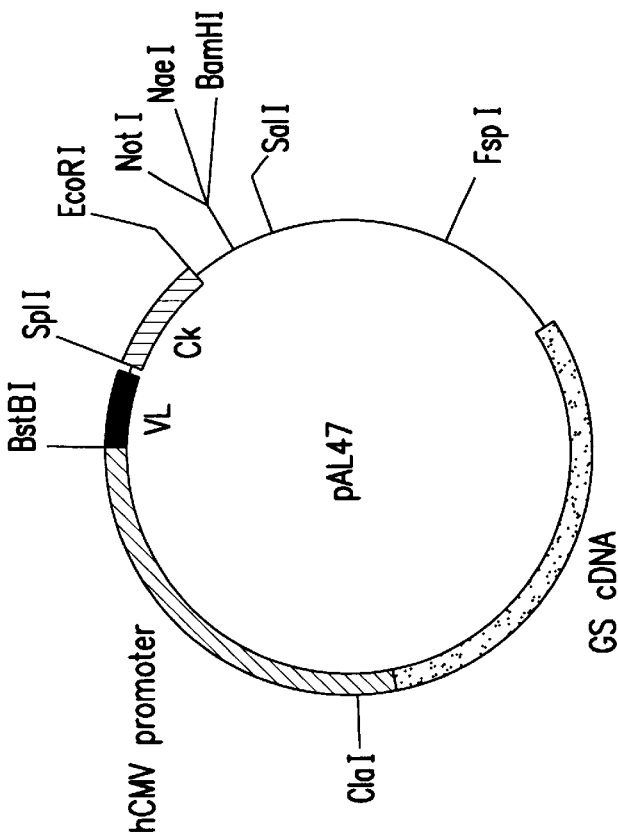
FIG. 20 is a schematic diagram of plasmid pAL47.

The nucleotide sequences coding for gH1 and gH2 were cloned as HindIII-ApaI fragments into plasmid pMRR014 (FIG. 8) to produce plasmids pAL51 and pAL52 (FIGS. 17 and 18 respectively).

Figure 19:
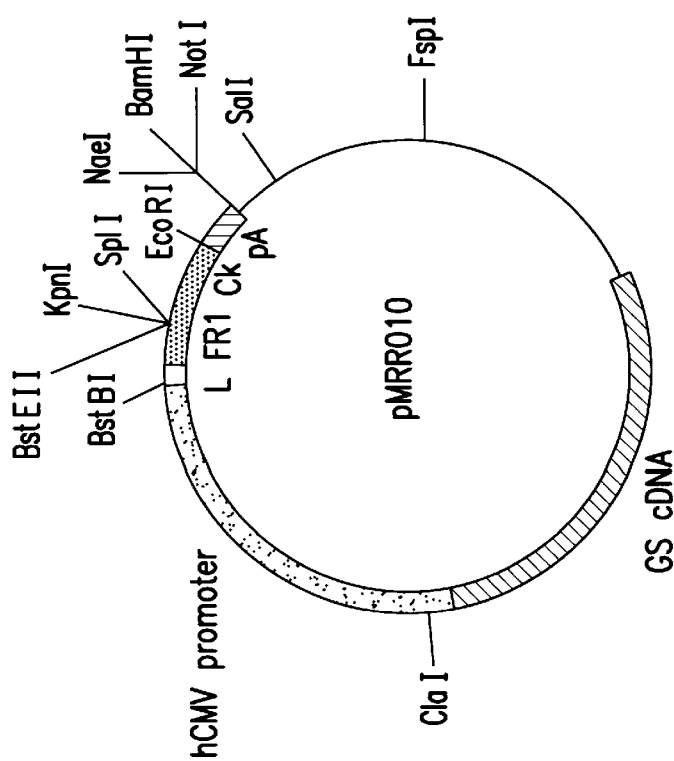
FIG. 19 is a schematic diagram of plasmid pMRR010.
Figure 21:
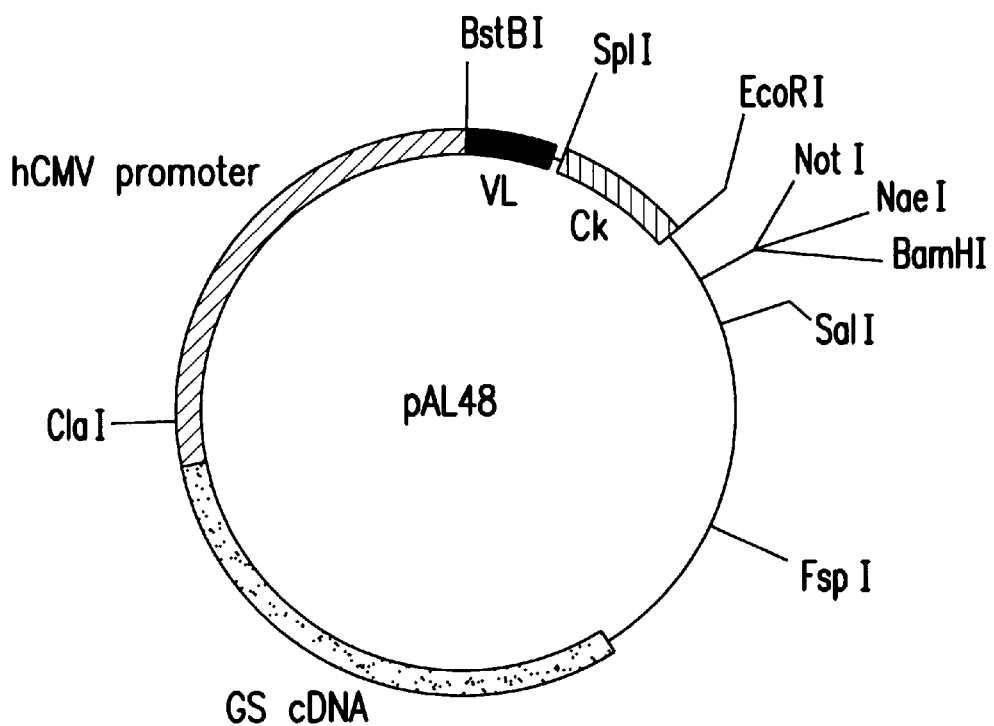
FIG. 21 is a schematic diagram of plasmid pAL48.
Figure 22:
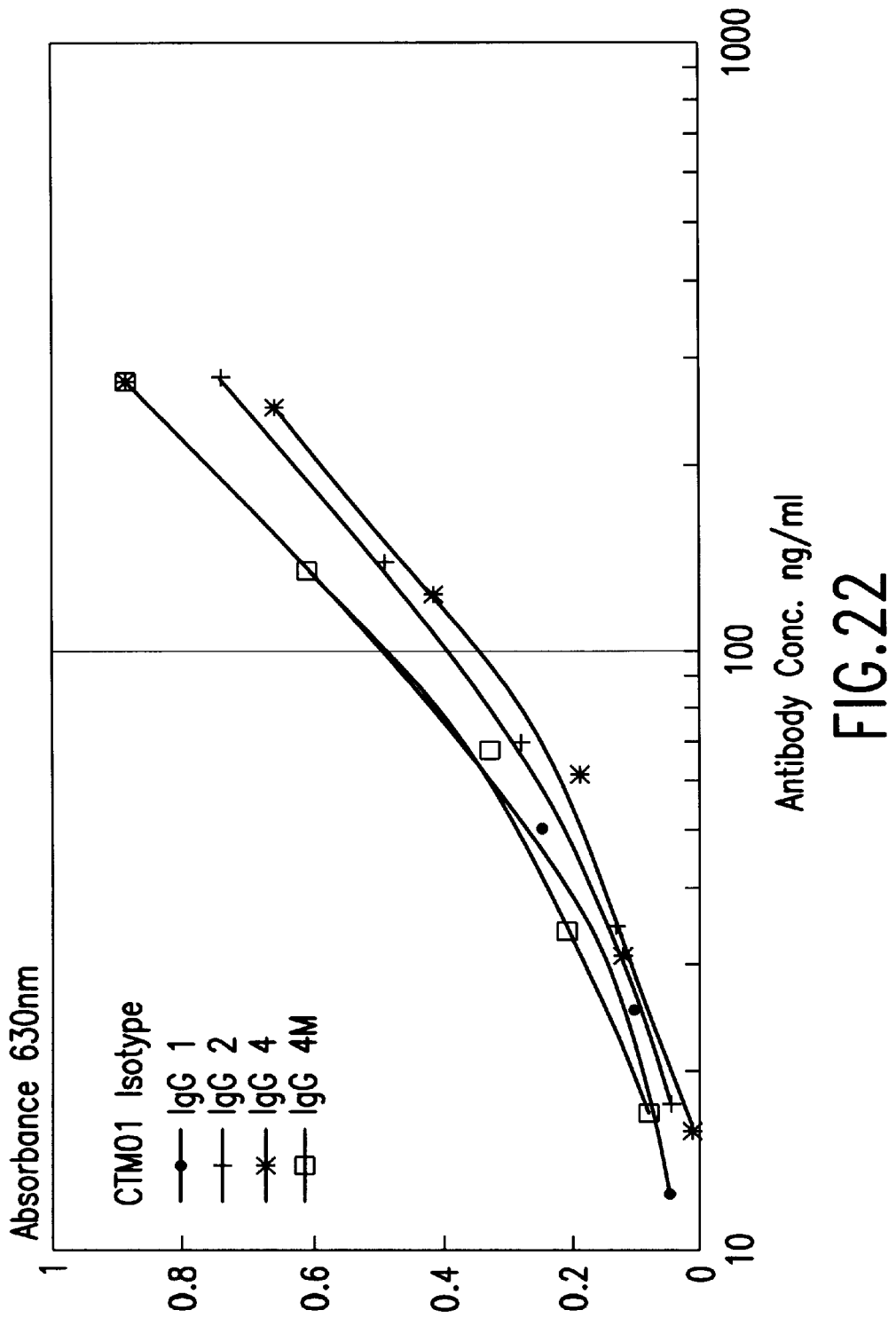
FIG. 22 is a graph of a direct binding ELISA on transiently expressed chimeric antibodies.
Figure 23:
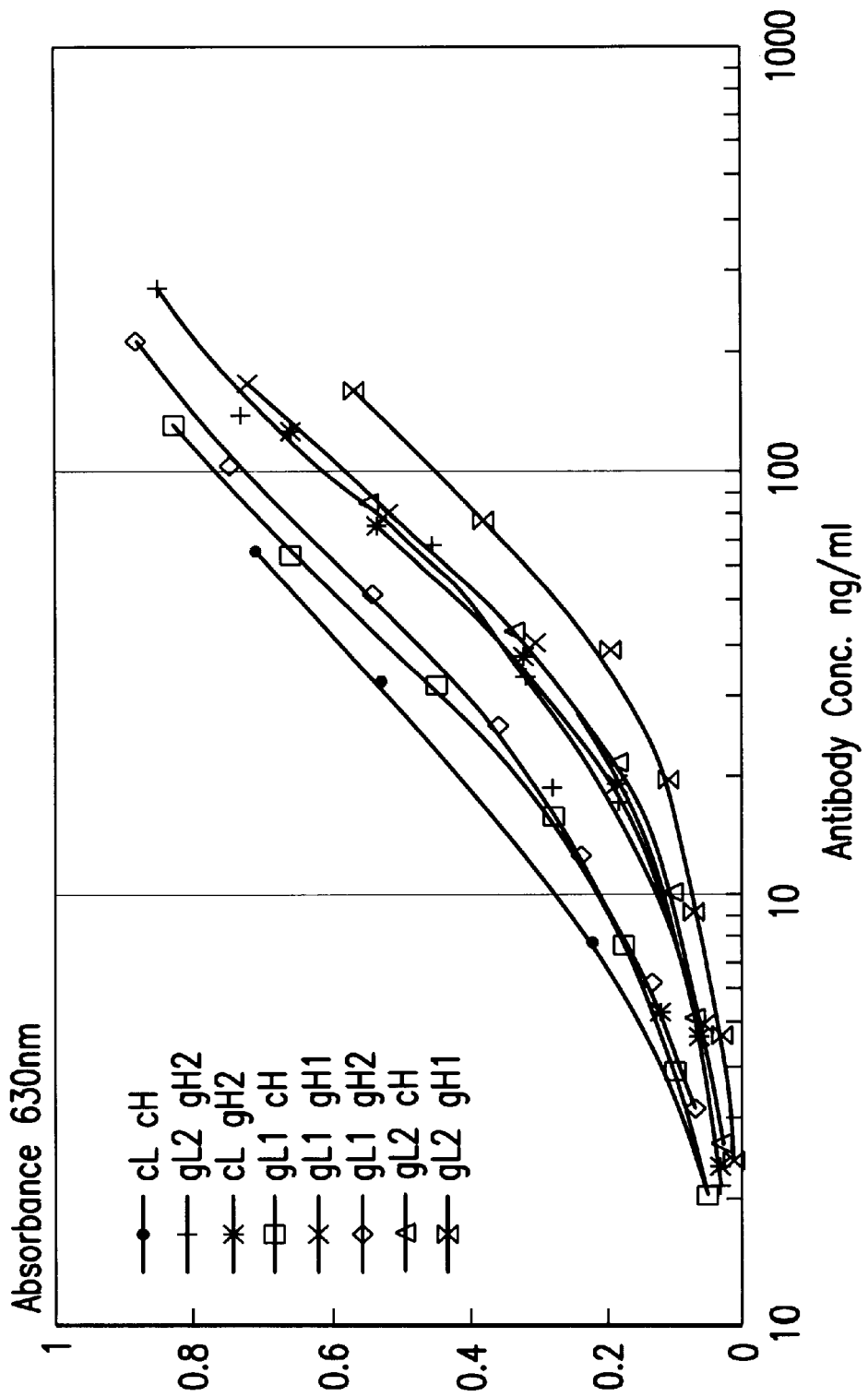
FIG. 23 is a graph of a direct binding ELISA on transiently expressed CDR-grafted antibodies.
Figure 24:
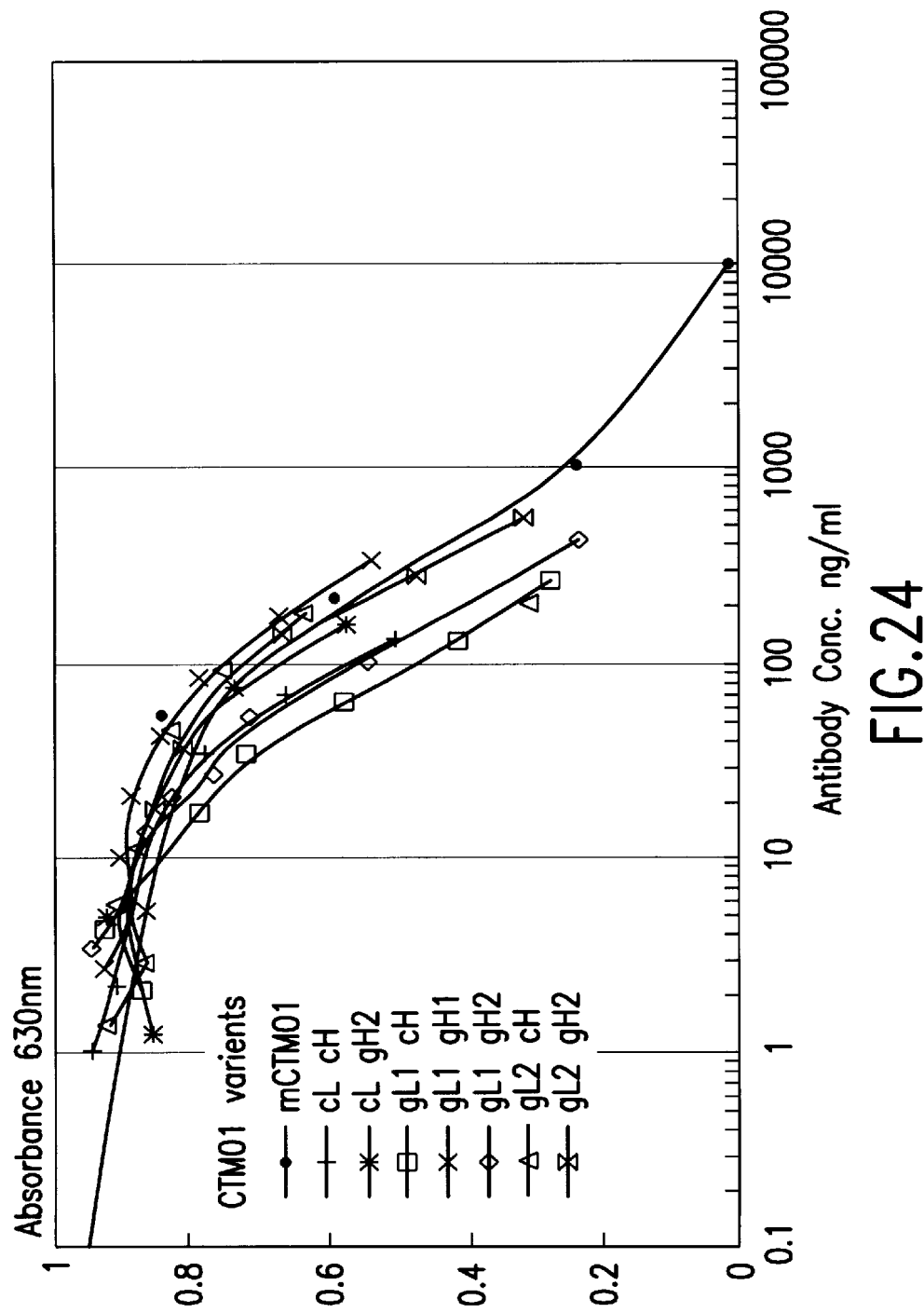
FIG. 24 is a graph of a competition EIA on transiently expressed chimeric and CDR-grafted antibodies.

The nucleotide sequences coding for gL1 and gL2 were cloned as HindIII-ApaI fragments into plasmid pMRR010 (FIG. 19) to produce plasmids pAL47 and pAL48 (FIGS. 20 and 21 respectively).

Transient Expression of Chimeric/Chimeric or CDR-grafted/Chimeric Antibodies

The following plasmids:

pHMC38, pHMC40, pHMC41 and pHMC42 and the following pairs of plasmids:

pAL47, pHMC33; pAL48, pHMC33; pAL51, pAL41; pAL52, pAL41;

and pAL48, pAL41;

were each transfected or cotransfected into CHO-L761h cells for transient expression.

Assembly ELISA assays on culture supernatants resulting from the single transfected cells showed that they contained assembled antibody.

The assembly ELISA assay for quantifying antibody yields used microwell plates coated with a goat $F(ab')_2$ anti-human IgGFc. Following incubation with transfected culture supernatants, bound chimeric or CDR-grafted antibody was revealed with a horseradish peroxidase (HRP)-conjugated murine anti-human IgK antibody using tetramethyl benzidine (TMB) as the substrate. Concentrations of chimeric or CDR-grafted whole antibody in the samples were interpolated from a calibration curve generated from serial dilutions of purified chimeric B72.3 g4 antibody (Colcher et al, Proc. Natl. Acad. Sci., USA, 86, 3833–3837, 1989).

Binding Activity Of Transiently Expressed Chimeric or CDR-grafted Antibodies

Direct binding ELISA assays for determining the binding activity of the transiently expressed antibodies were carried out as follows.

An affinity column was prepared by attaching the CT-M-01 MAb to a suitable chromatographic medium in conventional manner. In a first method, pooled human urine samples were applied directly to the affinity column. In a second method, human milk was subjected to low speed centrifugation to separate the cream from skimmed milk. The skimmed milk was then subjected to high speed centrifugation to produce an aqueous and a lipid component. The aqueous component was applied to the affinity column.

Once the affinity column was loaded, by either of the two methods, column fractions were eluted at high and low pHs, neutralized and assayed for reactivity with the CT-M-01 MAb. Fractions showing reactivity were pooled and dialyzed. The pooled fractions contained the polymorphic epithelial mucin (PEM) recognized by the CT-M-O1 MAb.

Microwell plates were coated with PEM obtained as described above. The microwells were then incubated with serial dilutions of culture supernatants. Binding of chimeric or CDR-grafted antibody was revealed and quantified by use of an HRP-conjugated murine anti-human IgK antibody.

The results of direct binding ELISA assays on the supernatants from singly transfected cells are shown in FIG. 22. These assays confirm that all the supernatants contained antibodies capable of binding to PEM. No significant differences in binding activity were observed.

The direct binding ELISA assays on the supernatants from doubly transifected cells confirmed that the supernatants contained antibodies capable of binding to PEM and that the chimeric/chimeric antibody bound better than any of the CDR-grafted/chimeric antibodies.

A competition binding assay was carried out using polystyrene beads coated with PEM obtained as described above. CT-M-O1 MAb was radiolabelled with 125I and was used to compete with the antibody produced by the pHMC40 (IgG1) transfected cells. The potency of the chimeric antibody was 84–102% that of the CT-M-O1 MAb.

Transient Expression of CDR-grafted/CDR-grafted Antibodies

The following pairs of plasmids:

pAL47, pAL51; pAL47, pAL52; pAL48, pAL51; and pAL48, pAL52;

were cotransfectecd into CHO-L761 cells.

Direct binding assays were carried out on the culture supernatants produced by the doubly transfected cell lines.

The results of these assays are shown in FIG. 23, together with some results for chimeric/CDR-grafted antibodies.

From all the direct binding assays referred to above, it can be determined that the order of binding activity of the various antibodies produced by transient expression is as follows:

cLcH3>gL1ch=gL1gH2>cLgH2=gL2H2=gL1gH1=gL2cH>gL2gH1.

(wherein:cL=chimeric light chain;

cH=chimeric heavy chain gL1=CDR-grafted light chain with lowest number of amino acid changes;

gL2=CDR-grafted light chain with highest number of amino acid changes;

gH1=CDR-grafted heavy chain with lowest number of amino acid changes;

gH2=CDR-grafted heavy chain with highest number of amino acid changes).

The more active variants (cLcH, gL1cH, gL1gH2 and gL2gH2) together with the CT-M-O1 MAb were tested in a competition enzyme immunoassay (EIA). Microwell plates were coated with PEM obtained as described above. The CT-M-O1 MAb was biotinylated and was used to compete with the four variants referred to above. Bound biotinylated CT-M-O1 MAb was revealed and quantified using a streptavidin-HRP conjugate and TMB.

The results of the competition EIA are shown in FIG. 24, which shows the same ranking of binding activity as set out above, except that the gL1cH combination shows greater activity than the cLcH combination.

It can thus be seen that chimeric, chimeric/CDR-grafted and CDR-grafted antibodies which recognize the same antigen as the CT-M-O1 MAb have successfully been produced.

In Vitro Cell Binding and Internalization of CDR-grafted CT-M-O1 Antibodies

Stable NSO cell lines expressing gL1gH2lgG2 CT-M-O1 (hereinafter hu1:CT-M-O1) and gL1gH2lgG4P CT-M-O1

(hereinafter hu:CT-M-O1) ant-body variants were made by transfecting into NSO cells by electroporation double gene expression plasmids assembled by ligating the large (7.8 kbp) Not1/BamH1 fragment of pAL47 to the 2.4 kbp Not1/Apa1 fragment from pAL52 and either a 1.9 Kbp BamH1/Apa1 (partial) fragment carrying the lgG2 constant domains or a 2kbp Apa1/BamH1 fragment carrying the lgG4P constant domains as appropriate.

Antibody, purified from the supernatant of each cultured cell line by protein-A sepharose chromatography was radio-labelled ($^{125}I$) and incubated using a conventional continuous exposure method with either MX-1 or MCF-7 breast carcinoma cells. Radiolabelled murine CT-M-O1 was used in all tests as a comparison. All antibodies were incubated at 2 mg/million cells. The total binding of antibodies to the cells and the peak net uptake of the antibodies by the cells was determined. With both cell lines each CDR grafted antibody exhibited better cinding and internalization than the murine form.

The invention also includes therapeutic compositions containing the hu:CT-M-01-drug conjugates of the invention and uses of such compositions in therapy.

Such therapeutic compositions typically comprise a hu:CT-M-01-drug conjugate according to the invention in combination with a pharmaceutically acceptable excipient, e.g. for in vivo use. Therapeutic use typically comprises administering an effective amount of the conjugate according to the invention to a human subject.

In the hu:CT-M-01, the heavy and light chain variable domains of the hu:CT-M-01 may comprise either the entire variable domains of the CT-M-01 MAb or may comprise framework regions of a human variable domain having grafted thereon one, two or all three of the CDRs of the CT-M-01 MAb. Thus, the hu:CT-M-01 may comprise a chimeric humanized antibody or a CDR-grafted humanized antibody.

When the hu:CT-M-01 is a CDR-grafted humanized antibody, in addition to the CDRs, specific variable region framework residues may be altered to correspond to non-human, i.e. the CT-M-01 mouse, residues. Preferably, the CDR-grafted hu:CT-M-01 MAbs include CDR-grafted humanized antibodies as defined in International Patent Application No. PCT/GB90/02017. The disclosure of PCT/GB90/02017 is incorporated herein by reference.

Preferably, the CDRs of the light chain correspond to the Kabat CDRs at CDR1 (residues 24–34) and CDR2 (residues 50–56) and to the structural loop residues (residues 91–96) or Kabat CDR residues (residues 89–97) in CDR3. (The residue designations given above and elsewhere in the present application are numbered according to the Kabat numbering system, Kabat et al., supra.) In addition, the light chain may have mouse CT-M-01 residues at one or more of residues 1, 2, 3, 36, 37, 45, 48, 49, 60, 63, 70, 84, 85, 87 and 108. In preferred embodiments, when the human framework used is EU, the light chain comprises Kabat CDRs at all of CDR1, CDR2, and CDR3 and preferably additional CT-M-01 residues at positions 3, 36, 37, 45, 48, 63 and 108, or especially additional CT-M-01 residues at positions 3, 36, 63 and 108 only.

Preferably, the CDRs of the heavy chain correspond to the Kabat CDRs at all of CDR1 (26 to 35), CDR2 (50 to 65), and CDR3 (94 to 100). In addition, the heavy chain may have mouse CT-M-01 residues at one or more of residues 2, 6, 23, 37, 48, 49, 67, 69, 73, 76, 78, 80, 88, 91 and 94. In particularly preferred embodiments, when the human framework used is EU, the heavy chain framework comprises additional CT-M-01 residues at positions 1, 37, 48, 49, 67, 69, 73, 76, 78, 80, 88, 91 and 94. In particularly preferred embodiments, when the human framework used is EU, the heavy chain framework comprises additional CT-M-01 residues at positions 1, 37, 71 and 73, and especially in addition at positions 48, 67 and 69.

In addition, EU has a particularly idiosyncratic J region between residues 103 to 113 and it may be useful to include the murine amino acids, a consensus human J region or a suitable combination of both at residues 103 to 108 inclusive. When the EU framework is used, preferably heavy chain residues 94, 103, 104, 105 and 107 are murine residues, since in the case of these residues, the murine sequence is more frequently found in human $V_H$ sequences than the EU residues.

The standard techniques of molecular biology may be used to prepare DNA sequences coding for CDR-grafted products such as hu:CT-M-01. Desired DNA sequences may be synthesized completely or in part using oligonucleotide synthesis techniques. Site-directed mutagensis and polymerase chain reaction (PCR) techniques may be used as appropriate. For example, oligonucleotide directed synthesis of a pre-existing variable domain region may be used. Enzymatic filling-in of gapped oligonucleotides using T4 DNA polymerase may be used.

Any suitable host cell/vector system may be used for expression of the DNA sequences coding for the chimeric or CDR-grafted heavy and light chains. Bacterial, e.g. *E. coli*, and other microbial systems may be used, in particular for expression of antibody fragments, e.g. Fv, Fab and Fab' fragments and single chain antibody fragments, e.g. single chain Fvs. Eucaryotic, e.g. mammalian host cell, expression systems may be used for production of larger chimeric or CDR-grafted antibody products, including complete antibody molecules. Suitable mammalian host cells include CHO cells and myeloma or hybridoma cell lines.

The following description of certain embodiments of the invention is provided by way of example only and is not to be regarded as placing any limitations on the scope of the protection claimed.

Synthesis of the 4-Mercapto-4-methyl-pentanoic Acid Disulfide Derivative of N-Acetyl Calicheamicin $\gamma_1^I$ To N-acetyl calicheamicin $\gamma_1^I$ at a concentration of 2 mg/mL in acetonitrile at −15° C. is added 5 molar equivalents of 4-mercapto-4-methyl-pentanoic acid and 6 molar equivalents of triethylamine. After 24 hours at −15° C. the reaction is checked by $C_{18}$-HPLC. If the reaction is incomplete, additional amounts of 4-mercapto-4-methyl-pentanoic acid and triethyl amine are added. Upon completion of the reaction the volatile organics are evaporated under reduced pressure and the crude product is chromatographed on Bio-Sil A using a gradient of 0 to 5% methanol in chloroform. Pure fractions as assessed by tlc are pooled and evaporated to a glass. The $^1$H-NMR of the product is similar to N-acetyl calicheamicin $\gamma_1^I$, but is missing the absorbance for —SSSMe and exhibits absorbances for the methylpentanoic acid moiety as expected. FAB-MS gives m/z=1478 (M+H) and 1500 (M+Na).

Synthesis of the Hydroxysuccinimide Derivative of 4-Mercapto-4-methyl-pentanoic Acid Disulfide of N-Acetyl Calicheamicin $\gamma_1^I$ To the 4-mercapto-4-methyl-pentanoic acid disulfide derivative of N-acetyl calicheamicin $\gamma_1^I$ described above at a concentration of 5 mg/mL in acetonitrile at ambient temperature is added 3 molar equivalents of N-hydroxy succinimide and 5 molar equivalents of 1-(3-dimethylamino-propyl)-3-ethylcarbodiimide hydrochloride. After 1 hour the reaction is checked by $C_{18}$-HPLC. If the reaction is incomplete, then additional 1-(3-dimethylaminopropyl)-3-ethylcarbodiimide hydrochloride is added. Upon completion of the reaction the volatile organics are evaporated under reduced pressure and the crude product is chromatographed on Bio-Sil A using a gradient of 0 to 5% methanol in chloroform. Pure fractions as assessed by tlc are pooled and stripped to a glass. The $^1$H-NMR is similar to that of the product described above, but with absorbances present for succinimide, as expected. FAB-MS gives m/z=1575 (M+H) and 1597 (M+Na).

Synthesis of a hu:CT-M-01 Conjugate Using the Hydroxysuccinimide Derivative of 4-Mercapto-4-methyl-pentanoic Acid Disulfide of N-Acetyl Calicheamicin $\gamma_1^I$ To hu:CT-M-01 in phosphate buffer at a pH of about 7.4 is added 2–6 molar equivalents of the hydroxysuccinimide derivative of 4-mercapto-4-methyl-pentanoic acid disulfide of N-acetyl calicheamicin $\gamma_1^I$, described above, in DMF such that the final concentration of DMF is 10–15%. After completion of the reaction (4–24 hours) the low-molecular-weight organic material is removed by, for example, passing through a desalting column using pH 7.4 phosphate buffer. The product is further purified by chromatography on a gel exclusion column and concentrated to give a monomeric product with an average loading of 1–3 molecules of calicheamicin derivative per molecule of antibody.

In vivo Tests for Antitumor Activity

Figure 25:
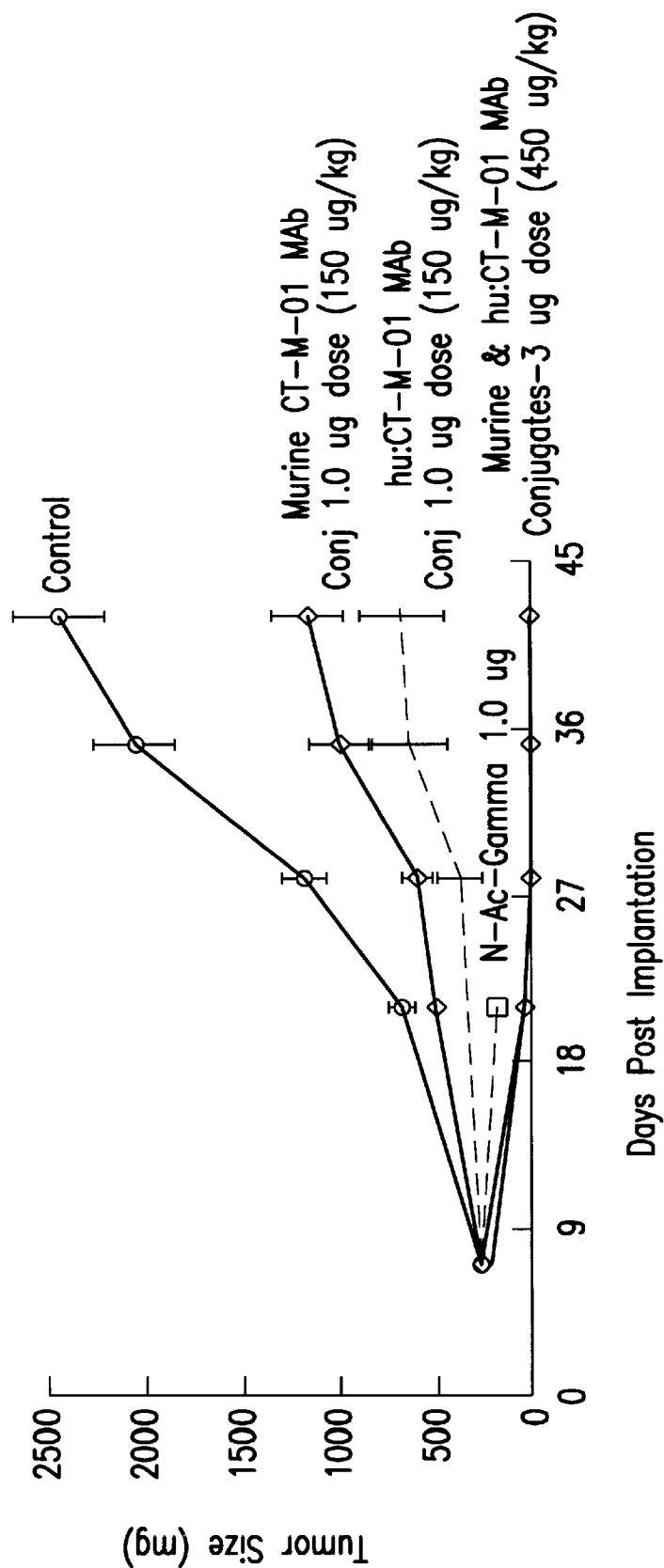
FIG. 25 is a graph comparing the effects on tumour size obtained by treating nude mice implanted with a human ovarian xenograft tumour with a humanised CDR grafted CT-M-01 and a murine CT-M-01 antibody each conjugated to the hydroxysuccinimide derivative of 4-mercapto-4-methyl-pentanoic acid disulphide of N-acetyl calicheamicin $\gamma_1^I$.

Description of Test for FIG. 25

The human ovarian xenograft tumor, OvCar3, implanted subcutaneously in nude mice was used as a test system to study the efficacy of the humanized and murine CT-M-01 conjugates in vivo. The NIH: OvCar-3, human ovary adenocarcinoma from ATCC (ATCC line # HTB 161) (Hamilton, T. C., et al. Cancer Res. 1983, 43, 5379), was adapted as an ascites tumor in this laboratory. The ascites was harvested from donor mice, and $8 \times 10^6$ cells were routinely implanted subcutaneously into athymic mice. The tumor was staged for 7 clays, to a size of >100 mg prior to inoculation with test samples. Tumors were implanted subcutaneously into athymic mice and test samples were inoculated intraperitoneally (IP) at several dose levels on a q 4 day×3 schedule, starting 8 days after tumor implantation in 6 mice per test group and 10 in each control group. Tumor mass was determined by measuring the tumor diameter once weekly during 42 days post tumor implantation. Significant antitumor activity was defined as a sustained 58% inhibition of mean tumor mass compared with untreated controls in groups with greater than 65% survivors. At both the 1 and 3 μg doses of drug equivalents (total dose of drug equivalent to 150 μg/kg and 450 μg/kg) the hu:CT-M-01 conjugate showed significant, inhibition of tumor growth. No deaths were noted in the 42 deay observation period in any test group. In all test groups, n=6, in the control group n=10, error bars=±Standard Error Mean for each data point

Figure 26:
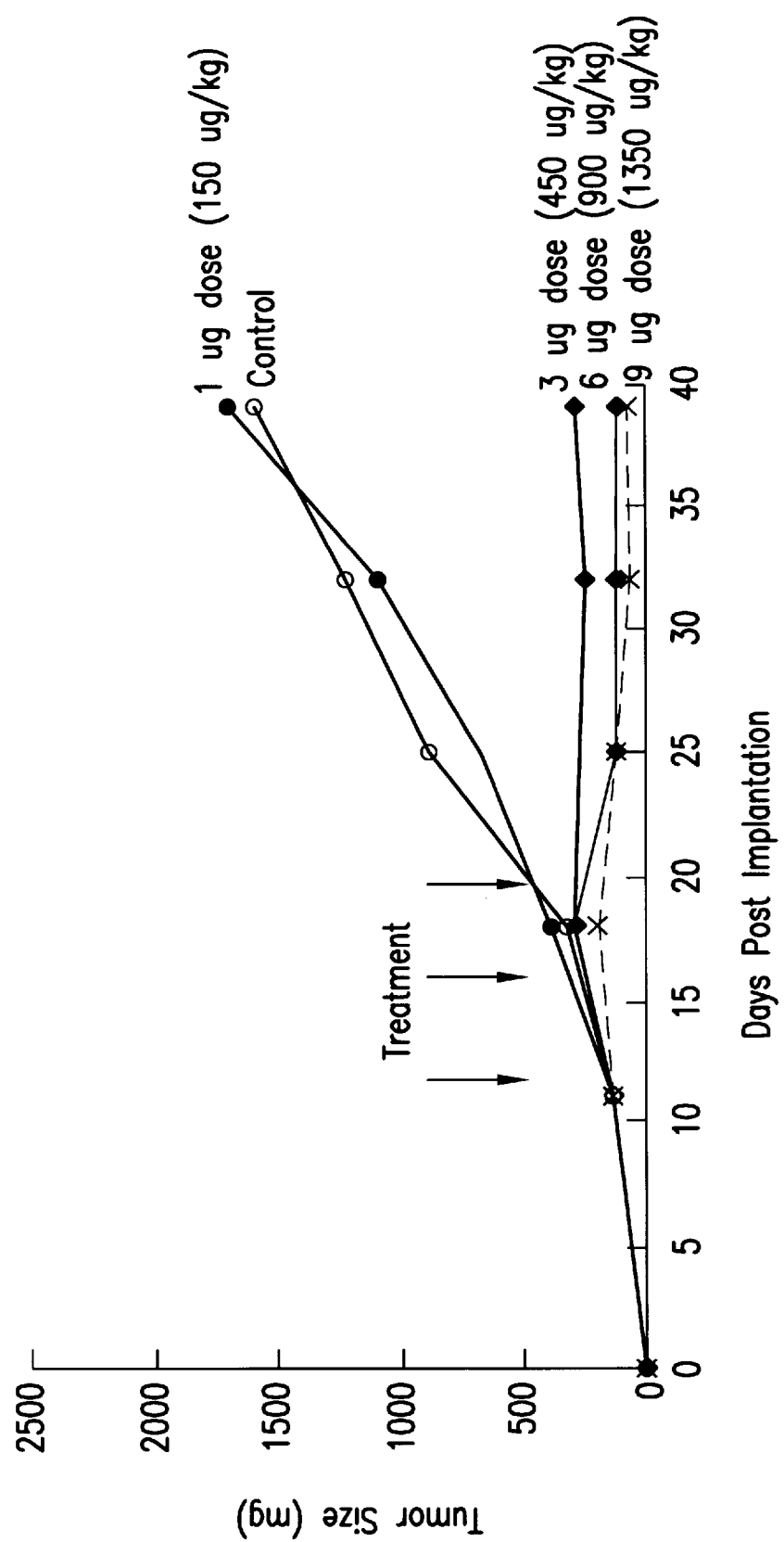
FIG. 26; is a graph showing the effects on tumor size obtained by treating nude midce implanted with a human breast xenograft tumor with a humanised CDR grafted CT-M-01 antibody conjugated to the hydroxysuccinimide derivative of 4-mercapto-4-methyl-pentanoic acid disulphide of N-acetyl calicheamicin $\gamma_1^I$.

Description of Test for FIG. 26

The human breast xenograft tumor, MX-1, implanted subcutaneously in nude mice was used as a test system to study the efficacy of the humanized CT-M-01 conjugate in vivo. MX-1 is a ductal cell carcinoma obtained as xenograft transplants from the Division of Cancer Treatment and the Division of Cancer Prevention of the National Cancer Institute. The tumor was carried as fragments in donor mice and for implantation into test mice, the tumors were removed and cut into 1 mm fragments, five of which were implanted subcutaneously in each test mouse. Tumors were staged and animals sorted on day 10, when the tumors reached a size of approximatley 100 mg. Injections were initated one day after staging (day 11 after implantation). Test samples were inoculated intraperitoneally (IP) at several dose levels on a q 4 day×3 schedule with 5 mice per test group and 10 the control group. Tumor mass was determined by measuring the tumor diameter once weekly during 39 days post tumor implantation, with the first measurement made on first treatment day (day 11). Significant antitumor activity was defined as a sustained 58% inhibition of mean tumor mass compared with untreated controls in groups with greater than 65% survivors. At doses of 3, 6 and 9 μg of drug equivalents (given ×3 for a total doses ranging from 150 to 1350 μg/kg), the hu:CT-M-01 conjugate showed significant inhibition of tumor growth. One death was noted in the 39 day observation period in the 6 ug test group. In all test groups, n=5, in the control group n=10, error bars= ±Standard Error Mean for each data point.

The described conjugates are useful for inhibiting the growth of unwanted cells which is an important part of the invention. Accordingly, the invention also includes pharmaceutical compositions, most preferably a parenteral composition suitable for injection into the body of a warm-blooded mammal. Such compositions are formulated by methods which are commonly used in pharmaceutical chemistry. The conjugates are acceptably soluble in physiologically-acceptable fluids, such as physiological saline solutions and other aqueous solutions which can safely be administered parenterally.

Products for parenteral administration are often formulated and distributed in solid, preferably freeze-dried form, for reconstitution immediately before use. Such formulations are useful compositions of the present invention. Their preparation is well understood by pharmaceutical chemists; in general, they comprise mixtures of inorganic salts, to confer isotonicity, and dispersing agents, such as sucrose, to allow the dried preparation to dissolve quickly upon reconstitution. Such formulations are reconstituted with highly purified water or physiologically acceptable buffers to a known concentration, based on the drug.

The optimum dosage and administration schedule of conjugates of the invention must be determined by the treating physician, in light of the patient's condition.

It is customary, of course, to administer cytotoxic drugs in the form of divided doses, with intervals of days or weeks between each series of doses. The conjugates are effective over a wide dosage range, and dosages per week will usually fall within the range from about 1 to about 10,000 μg/m² of drug, more preferably in the range from about 10 to about 200 μg/m².

It will be appreciated that the present invention has been described above by way of example only and that modifications of detail can be made within the scope and spirit of the invention.

We claim:

1. A cytotoxic drug conjugate of formula:

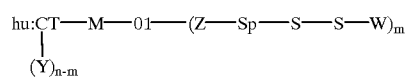

wherein
hu:CT-M-01 is a humanized monoclonal antibody reactive to human milk fat globule, its antigen-recognizing fragments, or its chemically manipulated counterparts;
Y is a side-chain amino, carboxyl, or thiol group of a protein, an aldehyde derived from glycoprotein residues, or an amidoalkylthio group;

n is from 1 to 100;

m is 0.1 to 15;

Z is —CONH—, —CONHN=CH—, —CONHNHCH$_2$—, —NHCSNHN=CH—, —NHCH$_2$—, —N=CH—, —CO$_2$—, —NHCH$_2$CO$_2$—,

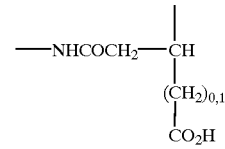

-continued

—SS—,

[chemical structure: thioether-succinimide]

[chemical structure: pyridine with acetoxymethyl and thioethyl substituents], or

[chemical structure: cyclopentanedione with CH₂O, CH₃ and S— substituents]

Sp is a straight or branched-chain divalent or trivalent ($C_1$–$C_{18}$) alkyl radical, divalent or trivalent aryl or heteroaryl radical, divalent or trivalent ($C_3$–$C_{18}$) cycloalkyl or heterocycloalkyl radical, divalent or trivalent aryl- or heteroaryl-alkyl ($C_1$–$C_{18}$) radical, divalent or trivalent cycloalkyl- or heterocycloalkyl-alkyl ($C_1$–$C_{18}$) radical or divalent or trivalent ($C_2$–$C_{18}$) unsaturated alkyl radical, wherein when Sp is a trivalent radical, Sp can be additionally substituted by amino, alkylamino, arylamino, heteroarylamino, carboxyl, lower alkoxy, hydroxy, thiol, or lower alkylthio groups; and W is an antitumor antibiotic designated as LL-E33288$\alpha_1^{Br}$, $\alpha_1^I$, $\alpha_2^{Br}$, $\alpha_2^I$, $\alpha_3^{Br}$, $\alpha_3^I$, $\alpha_4^{Br}$, $\beta_1^{Br}$, $\beta_1^I$, $\beta_2^{Br}$, $\beta_2^I$, $\gamma_1^{Br}$, $\gamma_1^I$, $\delta_1^I$, the iodo or bromo pseudoaglycones, their dihydro or N-acyl counterparts, BBM-1675, FR-900405, FR-900406, PD114759, PD115028, CL-1577A, CL-1577B, CL-1577D, CL-1577E, CL-1724, or their N-acetyl counterparts, from which the CH₃—S—S group has been displaced.

2. A cytotoxic drug conjugate according to claim 1, wherein

Sp is a straight or branched-chain divalent or trivalent ($C_2$–$C_{10}$) alkyl radical, or divalent or trivalent aryl- or heteroarylalkyl ($C_2$–$C_5$) radical, wherein when Sp is a trivalent radical, it can be additionally substituted by amino, heteroarylamino, hydroxy, or thiol groups;

Y is a side-amino group on the antibody, or an aldehyde generated by oxidation of the carbohydrate groups of the antibody; and Z is —CONH—, —CONHN=CH—, —CONHNHCH₂—, or

—NHCOCH₂—CH
         |
         (CH₂)₀,₁
         |
         CO₂H .

3. A cytotoxic drug conjugate according to claim 1, wherein W is the antitumor antibiotic designated LL-E33288γ₁ᴵ.

4. A cytotoxic drug conjugate according to claim 1, wherein W is the antitumor antibiotic designated LL-E33288α₂ᴵ.

5. A cytotoxic drug conjugate according to claim 1, wherein W is the antitumor antibiotic designated LL-E33288α₃ᴵ.

6. A cytotoxic drug conjugate according to claim 1, wherein W is the antitumor antibiotic designated N-acyl LL-E33288γ₁ᴵ.

7. A cytotoxic drug conjugate according to claim 1, wherein W is the antitumor antibiotic designated iodo LL-E33288 pseudoaglycone.

8. A cytotoxic drug conjugate according to claim 1, wherein Sp is —CH₂CH₂—, Y is —NH₂, Z is —CONH—, and m is 0.5 to 15.

9. A cytotoxic drug conjugate according to claim 1, wherein Sp is —CH₂CH(CH₃)—, Y is —NH₂, Z is —CONH—, and m is 0.5 to 15.

10. A cytotoxic drug conjugate according to claim 1, wherein Sp is —CH₂C(CH₃)₂—, Y is —NH₂, Z is —CONH—, and m is 0.5 to 15.

11. A cytotoxic drug conjugate according to claim 1, wherein Sp is

—(CH₂)₂—[phenyl]—

Y is —NH₂, Z is —CONH—, and m is 0.5 to 15.

12. A cytotoxic drug conjugate according to claim 1, wherein Sp is —CH₂CH₂—, Y is —CHO, Z is —CONHN=CH—, and m is 0.1 to 10.

13. A cytotoxic drug conjugate according to claim 1, wherein Sp is —CH₂CH₂—, Y is —CHO, Z is —CONHNHCH₂—, and m is 0.1 to 10.

14. A cytotoxic drug conjugate according to claim 1, wherein Sp is —CH₂CH(CH₃)—, Y is —CHO, Z is —CONHN=CH—, and m is 0.1 to 10.

15. A cytotoxic drug conjugate according to claim 1, wherein Sp is —CH₂CH(CH₃)—, Y is —CHO, Z is —CONHNHCH₂—, and m is 0.1 to 10.

16. A cytotoxic drug conjugate according to claim 1, wherein Sp is —CH₂C(CH₃)₂—, Y is —CHO, Z is —CONHN=CH—, and m is 0.1 to 10.

17. A cytotoxic drug conjugate according to claim 1, wherein Sp is —CH₂C(CH₃)₂—, Y is —CHO, Z is —CONHNHCH₂—, and m is 0.1 to 10.

18. A cytotoxic drug conjugate according to claim 1, wherein Sp is

—(CH₂)₂—[phenyl]—

Y is —CHO, Z is —CONHN=CH—, and m is 0.1 to 10.

19. A cytotoxic drug conjugate according to claim 1, wherein Sp is

—(CH₂)₂—[phenyl]—

Y is —CHO, Z is —CONHNCH₂—, and m is 0.1 to 10.

20. A cytotoxic drug conjugate according to claim 1, wherein Sp is

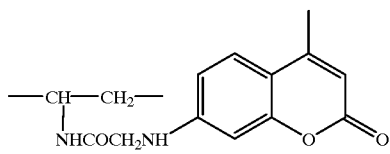

Y is —CHO, Z is —CONHN=CH—, and m is 0.1 to 10.

21. A cytotoxic drug conjugate according to claim 1, wherein Sp is

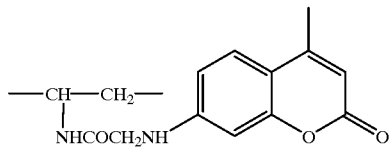

Y is —CHO, Z is —CONHNCH$_2$—, and m is 0.1 to 10.

22. A cytotoxic drug conjugate according to claim 12, wherein W is LL-E33288$\gamma_1^I$.

23. A cytotoxic drug conjugate according to claim 13, wherein W is LL-E33288$\alpha_3^I$.

24. A cytotoxic drug conjugate according to claim 8, wherein W is N-acyl LL-E33288$\gamma_1^I$.

25. A cytotoxic drug conjugate according to claim 9, wherein W is N-acyl LL-E33288$\gamma_1^I$.

26. A cytotoxic drug conjugate according to claim 10, wherein W is N-acyl LL-E33288$\gamma_1^I$.

27. A cytotoxic drug conjugate according to claim 18, wherein W is N-acyl LL-E33288$\gamma_1^I$.

28. A pharmaceutical composition for inhibiting the growth of cells, comprising an effective cell growth-inhibiting amount of the cytotoxic drug conjugate of claim 1 and a parenterally-administrable medium.

29. A method of inhibiting the growth of cells in a mammal comprising administering the cytotoxic drug conjugate of claim 1 to a mammal.

* * * * *

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
      (A) LENGTH: 416 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1..416

(xi) SEQUENCE DESCRIPTION: SEQ ID NO:1:

```
ATG GAA TGG AGC TGG GTC TTT CTC TTC TTC CTG TCG GTA ACC ACA GGT        48
Met Glu Trp Ser Trp Val Phe Leu Phe Phe Leu Ser Val Thr Thr Gly
  1               5                  10                  15

GTC CAT TGC CAG ATC CAG CTG CAG CAG TCT GGA CCT GAG CTG GTG AAG        96
Val His Cys Gln Ile Gln Leu Gln Gln Ser Gly Pro Glu Leu Val Lys
                 20                  25                  30

CCT GGG GCT TCA GTG AAG ATA TCC TGC AAG GCT TCT GGC TAC ACC TTC       144
Pro Gly Ala Ser Val Lys Ile Ser Cys Lys Ala Ser Gly Tyr Thr Phe
             35                  40                  45

ACT GAC TAC TAT ATA AAC TGG ATG AAG CAG AAG CCT GGA CAG GGA CTT       192
Thr Asp Tyr Tyr Ile Asn Trp Met Lys Gln Lys Pro Gly Gln Gly Leu
 50                  55                  60

GAG TGG ATT GGA TGG ATT GAT CCT GGA AGC GGT AAT ACT AAG TAC AAT       240
Glu Trp Ile Gly Trp Ile Asp Pro Gly Ser Gly Asn Thr Lys Tyr Asn
 65                  70                  75                  80

GAG AAG TTC AAG GGC AAG GCC ACA TTG ACT GTA GAC ACA TCC TCC AGC       288
Glu Lys Phe Lys Gly Lys Ala Thr Leu Thr Val Asp Thr Ser Ser Ser
                 85                  90                  95

ACA GCC TAC ATG CAG CTC AGC AGC CTG ACA TCT GAG GAC ACT GCT GTC       336
Thr Ala Tyr Met Gln Leu Ser Ser Leu Thr Ser Glu Asp Thr Ala Val
            100                 105                 110

TAT TTC TGT GCA AGA GAG AAA ACG ACC TAT TAC TAT GCT ATG GAC TAC       384
Tyr Phe Cys Ala Arg Glu Lys Thr Thr Tyr Tyr Tyr Ala Met Asp Tyr
        115                 120                 125

TGG GGT CAA GGA ACC TCA GTC ACT GTC TCC  GC                           416
Trp Gly Gln Gly Thr Ser Val Thr Val Ser Ala
        130                 135
```

(2) INFORMATION FOR SEQ ID NO:2:

(i) SEQUENCE CHARACTERISTICS:
      (A) LENGTH: 138 amino acids
      (B) TYPE: amino acid
      (D) TOPOLOGY: linear (ii) MOLECULE TYPE: protein (xi) SEQUENCE DESCRIPTION: SEQ ID NO:2:

```
Met Glu Trp Ser Trp Val Phe Leu Phe Phe Leu Ser Val Thr Thr Gly
  1               5                  10                  15

Val His Cys Gln Ile Gln Leu Gln Gln Ser Gly Pro Glu Leu Val Lys
                 20                  25                  30

Pro Gly Ala Ser Val Lys Ile Ser Cys Lys Ala Ser Gly Tyr Thr Phe
             35                  40                  45
```

```
Thr Asp Tyr Tyr Ile Asn Trp Met Lys Gln Lys Pro Gly Gln Gly Leu
         50                  55                  60

Glu Trp Ile Gly Trp Ile Asp Pro Gly Ser Gly Asn Thr Lys Tyr Asn
 65                  70                  75                  80

Glu Lys Phe Lys Gly Lys Ala Thr Leu Thr Val Asp Thr Ser Ser Ser
                 85                  90                  95

Thr Ala Tyr Met Gln Leu Ser Ser Leu Thr Ser Glu Asp Thr Ala Val
                100                 105                 110

Tyr Phe Cys Ala Arg Glu Lys Thr Thr Tyr Tyr Ala Met Asp Tyr
            115                 120                 125

Trp Gly Gln Gly Thr Ser Val Thr Val Ser
130                 135
```

(2) INFORMATION FOR SEQ ID NO:3:

(i) SEQUENCE CHARACTERISTICS:
        (A) LENGTH: 399 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..399

(xi) SEQUENCE DESCRIPTION: SEQ ID NO:3:

```
ATG AGG TGC CTA GCT GAG TTC CTG GGG CTG CTT GTG CTC TGG ATC CCT        48
Met Arg Cys Leu Ala Glu Phe Leu Gly Leu Leu Val Leu Trp Ile Pro
 1               5                  10                  15

GGA GCC ATT GGG GAT ATT GTG ATG ACT CAG GCT GCA CCC TCT GTT CCT        96
Gly Ala Ile Gly Asp Ile Val Met Thr Gln Ala Ala Pro Ser Val Pro
                 20                  25                  30

GTC ACT CCT GGA GAG TCA TTA TCC ATT TCC TGC AGG TCT AGT AAG AGT       144
Val Thr Pro Gly Glu Ser Leu Ser Ile Ser Cys Arg Ser Ser Lys Ser
             35                  40                  45

CTC CTT CAT AGT AAT GGC GAC ACT TTC TTG TAT TGG TTC CTG CAG AGG       192
Leu Leu His Ser Asn Gly Asp Thr Phe Leu Tyr Trp Phe Leu Gln Arg
         50                  55                  60

CCA GGC CAG TCT CCT CAA CTC CTG ATA TAT CGG ATG TCC AAC CTT GCC       240
Pro Gly Gln Ser Pro Gln Leu Leu Ile Tyr Arg Met Ser Asn Leu Ala
 65                  70                  75                  80

TCC GGA GTC CCA GAC AGG TTC AGT GGC AGT GGG TCA GGA ACT GCT TTC       288
Ser Gly Val Pro Asp Arg Phe Ser Gly Ser Gly Ser Gly Thr Ala Phe
                 85                  90                  95

ACA CTG AGA GTC AGT AGA GTG GAG GCT GAG GAT GTG GGT GTT TAT TAC       336
Thr Leu Arg Val Ser Arg Val Glu Ala Glu Asp Val Gly Val Tyr Tyr
            100                 105                 110

TGT ATG CAA CAT CTA GAA TAT CCT TTC ACG TTC GGT GCT GGG ACC AAG       384
Cys Met Gln His Leu Glu Tyr Pro Phe Thr Phe Gly Ala Gly Thr Lys
        115                 120                 125

CTG GAG CTG AAA CGG                                                   399
Leu Glu Leu Lys Arg
        130
```

(2) INFORMATION FOR SEQ ID NO:4:

(i) SEQUENCE CHARACTERISTICS:
        (A) LENGTH: 133 amino acids
        (B) TYPE: amino acid
        (D) TOPOLOGY: linear (ii) MOLECULE TYPE: protein (xi) SEQUENCE DESCRIPTION: SEQ ID NO:4:

Met Arg Cys Leu Ala Glu Phe Leu Gly Leu Leu Val Leu Trp Ile Pro
 1               5                  10                  15

Gly Ala Ile Gly Asp Ile Val Met Thr Gln Ala Ala Pro Ser Val Pro
             20                  25                  30

Val Thr Pro Gly Glu Ser Leu Ser Ile Ser Cys Arg Ser Ser Lys Ser
         35                  40                  45

Leu Leu His Ser Asn Gly Asp Thr Phe Leu Tyr Trp Phe Leu Gln Arg
     50                  55                  60

Pro Gly Gln Ser Pro Gln Leu Leu Ile Tyr Arg Met Ser Asn Leu Ala
 65                  70                  75                  80

Ser Gly Val Pro Asp Arg Phe Ser Gly Ser Gly Ser Gly Thr Ala Phe
                 85                  90                  95

Thr Leu Arg Val Ser Arg Val Glu Ala Glu Asp Val Gly Val Tyr Tyr
            100                 105                 110

Cys Met Gln His Leu Glu Tyr Pro Phe Thr Phe Gly Ala Gly Thr Lys
            115                 120                 125

Leu Glu Leu Lys Arg
            130

(2) INFORMATION FOR SEQ ID NO:5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 8..28

(xi) SEQUENCE DESCRIPTION: SEQ ID NO:5:

GGTGGCG GTA ACC ACA GGT GTC CAG TCA                                    28
        Val Thr Thr Gly Val Gln Ser
         1               5

(2) INFORMATION FOR SEQ ID NO:6:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:6:

Val Thr Thr Gly Val Gln Ser
 1               5

(2) INFORMATION FOR SEQ ID NO:7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
AGTGGCAGAG AAGTCGGAGT TGCTTCCCGG GTAGAC                                      36

(2) INFORMATION FOR SEQ ID NO:8:

(i) SEQUENCE CHARACTERISTICS:
        (A) LENGTH: 50 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 15..50

(xi) SEQUENCE DESCRIPTION: SEQ ID NO:8:

AGCTTGCCGC CACC ATG GAA TGG AGC TGG GTC TTT CTC TTC TTC CTG TCG              50
             Met Glu Trp Ser Trp Val Phe Leu Phe Phe Leu Ser
             1               5                  10

(2) INFORMATION FOR SEQ ID NO:9:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:9:

Met Glu Trp Ser Trp Val Phe Leu Phe Phe Leu Ser
 1               5                  10

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GCGCGCAAGC TTGCCGCCAC C                                                      21

(2) INFORMATION FOR SEQ ID NO:11:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

TCTCAGATTC AGCTGGTGCA GTCTGGAGCA GAGGTGAAGA AGCCTGGATC TTCTGTGAAG            60

GTGTCTTGTA AGGCATCTGG ATACACCTTC ACCGAC                                      96

(2) INFORMATION FOR SEQ ID NO:12:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:12:

TGGATTGACC CTGGATCTGG AAATACAAAG TACAATGAGA AGTTCAAGGG AAGAGTGACA    60

ATTACAGTGG ACACATCCAC GAATACCGCC TACATG    96

(2) INFORMATION FOR SEQ ID NO:13:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GAGAAGACCA CCTACTACTA CGCAATGGAC TACTGGGGAC AGGGAACACT GGTGACAGTG    60

TCTTCTGCCT CAACGAAGGG CCCGCGCGC    89

(2) INFORMATION FOR SEQ ID NO:14:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CTGCACCAGC TGAATCTGAG AATGGACTCC TGTAGTTACT GACAGGAAGA AGAGAAAGAC    60

CCAGCTCCAT TCCATGGTGG CGGCAAGCTT GCGCGC    96

(2) INFORMATION FOR SEQ ID NO:15:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

TCCAGATCCA GGGTCAATCC ATCCCATCCA CTCGAGTCCC TGTCCAGGTG CCTGTCTCAT    60

CCAATTAATG TAGTAGTCGG TGAAGGTGTA TCCAGA    96

(2) INFORMATION FOR SEQ ID NO:16:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

GTAGTAGTAG GTGGTCTTCT CTCTTGCACA GAAGTAGAAT GCTGTGTCCT CAGATCTCAG    60

AGAAGACAGC TCCATGTAGG CGGTATTCGT GGA    93

(2) INFORMATION FOR SEQ ID NO:17:

(i) SEQUENCE CHARACTERISTICS:
        (A) LENGTH: 21 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

GCGCGCGGGC CCTTCGTTGA G                                               21

(2) INFORMATION FOR SEQ ID NO:18:

(i) SEQUENCE CHARACTERISTICS:
        (A) LENGTH: 139 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:18:

Met Glu Trp Ser Trp Val Phe Leu Phe Phe Leu Ser Val Thr Thr Gly
 1               5                  10                  15

Val His Ser Gln Ile Gln Leu Val Gln Ser Gly Ala Glu Val Lys Lys
             20                  25                  30

Pro Gly Ser Ser Val Lys Val Ser Cys Lys Ala Ser Gly Tyr Thr Phe
         35                  40                  45

Thr Asp Tyr Tyr Ile Asn Trp Met Arg Gln Ala Pro Gly Gln Gly Leu
     50                  55                  60

Glu Trp Met Gly Trp Ile Asp Pro Gly Ser Gly Asn Thr Lys Tyr Asn
 65                  70                  75                  80

Glu Lys Phe Lys Gly Arg Val Thr Ile Thr Val Asp Thr Ser Thr Asn
                 85                  90                  95

Thr Ala Tyr Met Glu Leu Ser Ser Leu Arg Ser Glu Asp Thr Ala Phe
            100                 105                 110

Tyr Phe Cys Ala Arg Glu Lys Thr Thr Tyr Tyr Ala Met Asp Tyr
        115                 120                 125

Trp Gly Gln Gly Thr Leu Val Thr Val Ser Ser
130                 135

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

GGACTGTTCG AAGCCGCCAC C                                               21

(2) INFORMATION FOR SEQ ID NO:20:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

TGGCTTACAG ATGCCAGATG CGATATCCAG ATGACTCAGA GTCCAAGTAC TCTCAGTGCC      60

```
AGTGTAGGTG ATAGGGTCAC C                                                    81

(2) INFORMATION FOR SEQ ID NO:21:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

GGTGACACCT TCCTCTATTG GTTCCAGCAG AAACCAGGTA AAGCCCCAAA GCTCCTCATG          60

TATAGGATGA GTAACCTCGC CAGTGGTGTA                                           90

(2) INFORMATION FOR SEQ ID NO:22:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

CAGCCAGATG ATTTCGCCAC TTATTATTGT ATGCAGCATC TCGAATATCC ATTCACTTTC          60

GGTCAGGGTA CTAAAGTAGA AGTAAAACGT ACGGGCCGG                                 99

(2) INFORMATION FOR SEQ ID NO:23:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

GCATCTGGCA TCTGTAAGCC ACAGCAGCAG GAGTCCGAGG ACTTGGGTGG GGACAGACAT          60

GGTGGCGGCT TCGAACAGTC C                                                    81

(2) INFORMATION FOR SEQ ID NO:24:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

CCAATAGAGG AAGGTGTCAC CGTTACTATG GAGGAGACTT TTACTACTCC TACAAGTGAT          60

GGTGACCCTA TCACCTACAC T                                                    81

(2) INFORMATION FOR SEQ ID NO:25:

(i) SEQUENCE CHARACTERISTICS:
        (A) LENGTH: 102 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:25:

AGTGGCGAAA TCATCTGGCT GGAGACTACT GATAGTGAGA GTGAACTCAG TACCACTACC        60

ACTACCACTG AATCTAGATG GTACACCACT GGCGAGGTTA CT                         102

(2) INFORMATION FOR SEQ ID NO:26:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

CCGGCCCGTA CGTTTTACTT C                                                 21

(2) INFORMATION FOR SEQ ID NO:27:

(i) SEQUENCE CHARACTERISTICS:
        (A) LENGTH: 133 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:27:

Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Thr Leu Ser
            20                  25                  30

Ala Ser Val Gly Asp Arg Val Thr Ile Thr Cys Arg Ser Ser Lys Ser
        35                  40                  45

Leu Leu His Ser Asn Gly Asp Thr Phe Leu Tyr Trp Phe Gln Gln Lys
    50                  55                  60

Pro Gly Lys Ala Pro Lys Leu Leu Met Tyr Arg Met Ser Asn Leu Ala
65                  70                  75                  80

Ser Gly Val Pro Ser Arg Phe Ser Gly Ser Gly Ser Gly Thr Glu Phe
                85                  90                  95

Thr Leu Thr Ile Ser Ser Leu Gln Pro Asp Asp Phe Ala Thr Tyr Tyr
            100                 105                 110

Cys Met Gln His Leu Glu Tyr Pro Phe Thr Phe Gly Gln Gly Thr Lys
        115                 120                 125

Val Glu Val Lys Arg
    130